United States Patent
Sutherland et al.

(10) Patent No.: US 12,351,545 B2
(45) Date of Patent: Jul. 8, 2025

(54) METHANOL PRODUCTION FROM METHANE UTILIZING A SUPPORTED CHROMIUM CATALYST

(71) Applicant: Chevron Phillips Chemical Company LP, The Woodlands, TX (US)

(72) Inventors: Jamie N. Sutherland, Kingwood, TX (US); James Hillier, Kingwood, TX (US); Gregory G. Hendrickson, Kingwood, TX (US); Max P. McDaniel, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/829,583

(22) Filed: Sep. 10, 2024

(65) Prior Publication Data

US 2025/0002434 A1 Jan. 2, 2025

Related U.S. Application Data

(62) Division of application No. 18/494,846, filed on Oct. 26, 2023, now Pat. No. 12,134,591.

(Continued)

(51) Int. Cl.
*C07C 29/48* (2006.01)
*B01J 23/26* (2006.01)
(Continued)

(52) U.S. Cl.
CPC ............... *C07C 29/48* (2013.01); *B01J 23/26* (2013.01); *B01J 35/617* (2024.01); *B01J 35/618* (2024.01);
(Continued)

(58) Field of Classification Search
CPC .......... C07C 29/48; C07C 31/04; C07C 29/09; B01J 23/26
See application file for complete search history.

(56) References Cited

U.S. PATENT DOCUMENTS 2,857,442 A 10/1958 Hay
2,913,492 A 11/1959 van der Voort
(Continued)

FOREIGN PATENT DOCUMENTS

CN 1150766 C 5/2004
CN 101264953 B 8/2010
(Continued)

OTHER PUBLICATIONS

Vaisman, E., et al., A fluidized bed photoreactor exploiting a supported photocatalyst with adsorption pre-concentration capacity, Journal of Applied Electrochemistry, 35:675-681 (Year: 2005).*

(Continued)

*Primary Examiner* — Yate' K Cutliff
(74) *Attorney, Agent, or Firm* — Merchant & Gould P.C.

(57) ABSTRACT

Processes for converting methane into methanol are disclosed in which methane, water, and a supported chromium (VI) catalyst are contacted with a light beam at a wavelength in the UV-visible spectrum in an oxidizing atmosphere in a single reactor to form a reaction product comprising methanol, followed by discharging a reactor effluent containing the reaction product from the single reactor, and then separating methanol from the reaction product. Processes to produce methanol using additional reactors also are described, as well as related methanol production systems.

27 Claims, 2 Drawing Sheets

Related U.S. Application Data

(60) Provisional application No. 63/381,580, filed on Oct. 31, 2022.

(51) Int. Cl.
  *B01J 35/61* (2024.01)
  *B01J 35/63* (2024.01)
  *C07C 29/09* (2006.01)
  *C07C 29/74* (2006.01)

(52) U.S. Cl.
  CPC .......... *B01J 35/633* (2024.01); *B01J 35/635* (2024.01); *C07C 29/09* (2013.01); *C07C 29/74* (2013.01); *C07C 2523/26* (2013.01)

(56) References Cited

U.S. PATENT DOCUMENTS

| | | | |
|---|---|---|---|
| 3,166,537 A | 1/1965 | Gregg | |
| 3,201,476 A | 8/1965 | Baker | |
| 3,242,099 A | 3/1966 | Manyik | |
| 3,694,422 A | 9/1972 | Long | |
| 3,857,901 A | 12/1974 | Dowden | |
| 4,248,735 A | 2/1981 | McDaniel | |
| 4,393,253 A | 7/1983 | Michaelson | |
| 4,460,756 A | 7/1984 | McDaniel | |
| 4,501,885 A | 2/1985 | Sherk | |
| 3,246,179 A | 4/1986 | Hawkins | |
| 4,588,790 A | 5/1986 | Jenkins, III | |
| 4,794,096 A | 12/1988 | Ewen | |
| 4,808,661 A | 2/1989 | Welborn, Jr. | |
| 4,918,249 A | 4/1990 | Durante et al. | |
| 5,220,080 A * | 6/1993 | Lyons ............... | C07C 29/50 568/910.5 |
| 5,345,011 A | 9/1994 | Durante | |
| 5,352,749 A | 10/1994 | Dechellis | |
| 5,414,157 A | 5/1995 | Durante | |
| 5,436,304 A | 7/1995 | Griffin | |
| 5,565,175 A | 10/1996 | Hottovy | |
| 5,575,979 A | 11/1996 | Hanson | |
| 5,576,259 A | 11/1996 | Hasegawa | |
| 5,635,438 A | 6/1997 | Cowfer | |
| 5,641,842 A | 6/1997 | McDaniel | |
| 5,720,858 A * | 2/1998 | Noceti ............... | C07C 29/48 204/157.9 |
| 5,739,220 A | 4/1998 | Shamshoum et al. | |
| 5,807,938 A | 9/1998 | Kaneko et al. | |
| 5,919,983 A | 7/1999 | Rosen et al. | |
| 5,955,557 A | 9/1999 | Machida | |
| 6,184,423 B1 | 2/2001 | Jen | |
| 6,239,235 B1 | 5/2001 | Hottovy | |
| 6,262,191 B1 | 7/2001 | Hottovy | |
| 6,310,167 B1 | 10/2001 | Kanzawa | |
| 6,380,444 B1 | 4/2002 | Bjerrum | |
| 6,518,375 B1 | 2/2003 | Monoi | |
| 6,825,377 B1 | 11/2004 | Beller | |
| 6,833,415 B2 | 12/2004 | Kendrick | |
| 7,112,643 B2 | 9/2006 | McDaniel | |
| 7,238,756 B2 | 7/2007 | Ehrman | |
| 7,294,599 B2 | 11/2007 | Jensen | |
| 7,304,199 B2 | 12/2007 | Xu | |
| 7,326,760 B2 | 2/2008 | Cann | |
| 7,407,591 B2 | 8/2008 | De Battisti | |
| 7,531,606 B2 | 5/2009 | Hendrickson | |
| 7,598,327 B2 | 10/2009 | Shaw | |
| 7,601,665 B2 | 10/2009 | McDaniel | |
| 7,648,940 B2 | 1/2010 | Holtcamp | |
| 7,649,062 B2 | 1/2010 | Matsunaga | |
| 7,884,163 B2 | 2/2011 | McDaniel | |
| 7,956,138 B2 | 6/2011 | Holtcamp | |
| 8,114,353 B2 | 2/2012 | Benham | |
| 8,114,946 B2 | 2/2012 | Yang | |
| 8,309,485 B2 | 11/2012 | Yang | |
| 8,623,973 B1 | 1/2014 | Mcdaniel | |
| 8,703,886 B1 | 4/2014 | Yang | |
| 8,822,608 B1 | 9/2014 | Bhandarkar | |
| 8,969,228 B2 | 3/2015 | Nazarpoor | |
| 9,006,367 B2 | 4/2015 | Mcdaniel | |
| 9,023,959 B2 | 5/2015 | Mcdaniel | |
| 9,096,699 B2 | 8/2015 | Mcdaniel | |
| 9,169,337 B2 | 10/2015 | Rohatgi | |
| 9,273,170 B2 | 3/2016 | Hlavinka | |
| 9,346,897 B2 | 5/2016 | Cui | |
| 9,394,393 B2 | 7/2016 | Hlavinka | |
| 9,540,457 B1 | 1/2017 | Ding | |
| 9,758,599 B2 | 9/2017 | Ding | |
| 9,796,798 B2 | 10/2017 | Praetorius | |
| 9,802,841 B2 | 10/2017 | Maruo | |
| 9,988,468 B2 | 6/2018 | Mcdaniel | |
| 10,000,594 B2 | 6/2018 | Hlavinka | |
| 10,213,766 B2 | 2/2019 | Praetorius | |
| 10,246,528 B2 | 4/2019 | Mcdaniel | |
| 10,287,369 B2 | 5/2019 | Schwerdtfeger | |
| 10,358,506 B2 | 7/2019 | Ding | |
| 10,435,527 B2 | 10/2019 | Praetorius | |
| 10,442,881 B2 | 10/2019 | Hlavinka | |
| 10,654,953 B2 | 5/2020 | Mcdaniel | |
| 10,662,266 B2 | 5/2020 | Mcdaniel | |
| 10,835,890 B2 | 11/2020 | Cann | |
| 10,858,459 B2 | 12/2020 | Mcdaniel | |
| 11,078,143 B2 | 8/2021 | Mcdaniel | |
| 11,180,435 B2 | 11/2021 | Cruz | |
| 11,440,864 B2 | 9/2022 | Mcdaniel | |
| 2004/0038811 A1 | 2/2004 | Parmaliana | |
| 2004/0059070 A1 | 3/2004 | Whitte | |
| 2004/0094478 A1 | 5/2004 | Nobel | |
| 2006/0241327 A1 | 10/2006 | Periana | |
| 2007/0219085 A1 | 9/2007 | De Battisti | |
| 2008/0032886 A1 | 2/2008 | Yeh | |
| 2012/0259144 A1 | 10/2012 | Stauffer | |
| 2013/0206453 A1 | 8/2013 | Fagrell | |
| 2014/0221692 A1 | 8/2014 | Netemeyer | |
| 2014/0275457 A1 | 9/2014 | Mcdanie | |
| 2015/0191554 A1 | 7/2015 | Mcdaniel | |
| 2017/0073439 A1 | 3/2017 | Ewart | |
| 2017/0088638 A1 | 3/2017 | Errun | |
| 2017/0274356 A1 | 9/2017 | Cann | |
| 2018/0079845 A1 | 3/2018 | Doufas | |
| 2019/0153129 A1 | 5/2019 | Mcdaniel | |
| 2019/0184389 A1 | 6/2019 | Neygandhi | |
| 2019/0308172 A1 | 10/2019 | Zou | |
| 2020/0086307 A1 | 3/2020 | Monwar | |
| 2020/0087430 A1 | 3/2020 | Clear | |
| 2020/0239605 A1 | 7/2020 | Mcdaniel | |
| 2021/0077981 A1 | 3/2021 | Cruz | |
| 2021/0078920 A1 | 3/2021 | Cruz | |
| 2021/0078926 A1 | 3/2021 | Barr | |
| 2021/0078927 A1 * | 3/2021 | McDaniel ............... | B01J 37/34 |
| 2022/0081370 A1 | 3/2022 | Monwar | |
| 2022/0356135 A1 | 11/2022 | Mcdaniel | |

FOREIGN PATENT DOCUMENTS

| | | |
|---|---|---|
| CN | 108203476 A | 6/2018 |
| CN | 108383686 | 8/2018 |
| CN | 106317267 B | 12/2018 |
| CN | 104774280 B | 9/2019 |
| CN | 106893015 B | 9/2019 |
| CN | 108439533 B | 7/2020 |
| CN | 107311263 B | 11/2020 |
| CN | 107108800 B | 3/2021 |
| DE | 2653666 A1 | 5/1978 |
| EP | 2374537 A2 | 10/2011 |
| JP | H05310601 A | 11/1993 |
| JP | H10182742 A | 7/1998 |
| JP | 2004244557 A | 9/2004 |
| JP | 2010132597 A | 6/2010 |
| JP | 2012101986 A | 5/2012 |
| RU | 2191625 C1 | 10/2002 |
| WO | 2005107943 A1 | 11/2005 |
| WO | 2015034816 A2 | 3/2015 |
| WO | 2017053534 A1 | 3/2017 |
| WO | 2018125690 A1 | 7/2018 |
| WO | 2020060888 A2 | 3/2020 |

(56) References Cited

FOREIGN PATENT DOCUMENTS

| WO | 2020060889 A2 | 3/2020 |
|---|---|---|
| WO | 2021055270 A1 | 3/2021 |
| WO | 2021055271 A1 | 3/2021 |
| WO | 2021055272 A1 | 3/2021 |

OTHER PUBLICATIONS

Office Action issued in corresponding CN Application No. 2021800624925, mailed on Aug. 31, 2024, 30 pp.

Awasthy, et al. "The Nature of the Transition Oxidation of Olefins by Chromium (VI)." JACS 91:4, Feb. 12, 1969, pp. 991-996.

Baker, et al., Oxidation of olefins by supported chromium oxide, The Journal of Organic Chemistry, vol. 33, No. 2, pp. 616-618 (Year 1968).

Barzan, et al., Ligands Make the Difference: Molecular Insights into CrVI/SiO2 Phillps Catalyst during Ethylene Polymerization, J. Am Chem. Soc , 2017, 139, 47, 17064-17073.

Brown, et al., "Mechanism of Initiation in the Phillips Ethylene Polymerization Catalyst: Redox Processes Leading to the Active Site", ACS Catal. 2015, 5, 5674-5583.

Brunauer, et al., "Adsorption of Gases in Multimolecular Layers", Journal of the American Chemical Society. 1938, vol. 60, pp. 309-319.

Cainelli, et al., "Reactivity and Structure Concepts in Organic Chemistry", vol. 19, "Chromium Oxidations in Organic Chemistry" Springer Verlag Berlin 1984, p. 8.

Chakrabarti, et al., "Operando Molecular Spectroscopy During ethylene Polymerization by supported CrOx/SiO2 Catalysts: Active Sites,Reaction Intermediates, and Structure-Activity Relationship", Top. Catal. 2016, 59 p. 725-739.

Christian Limberg, et al., "NMR Spectroscopic Evidence for Chromium(VI) Alkoxides Wih a-hydrogen Atoms," Chem. Commun., Dec. 31, 1998, pp. 225-226.

Cotton. F. Albert, "Advanced Inorganic Chemistry," Sixth Edition, cover page, title page, pp. ix-x, and book description, Mar. 30, 1999, John Wiley & Sons, Inc.

Cruz, et al., "Identification of the Starting Group on the Initial PE Chain Produced by Ohillips Catalyst", Macromolecules 2019, 52, 5750-5760.

Economy, et.al., "Supported Barium Chromate—A New Oxifation Catalyst", J. Calatysis, vol. 4, No. 4, Aug. 1, 1965, pp. 446-453.

Fendrick, et. al. "Actinacyclobutanes. Implementation of Thermochemically Based Strategies for the Ring-Opening Stoichiometric C—H Functionalization of Saturated and Olefinic Hydrocarbons", J. Am. Chem. Soc. 1986 108, 425-437.

Finch, "Reduction Studies on Supported Chromic Anhydride Catalysts," Journal of Catalysis, 43, 1976, pp. 111-121.

Floryan, et al., Strain Effect and Dual Initiation Pathway in Cr(III)/SiO2 Polymerization Catalysts from Amorphous Periodic Models, J. Catalysis 2017, 346, 50-56.

Gierada, et al., "Active sites formation and their transformations during ethylene polymerization by the Phillips CrOx/SiO2 catalyst", J, Catal., 2017. 352, 314-328.

Groppo, et al., "The Structure of Active Centers and the Ethylene Polymerization Mechanis, on the Cr/SiO2 Catalyst: A Frontier for the Characterization Method", Chem. Rev. 2005, 106, 115-183.

Halsey, "Physical Adsorption on Non-Uniform Surfaces," Journal Chem. Phys., vol. 16, Mar. 9, 1948, pp. 931-937.

Hawley's Condensed Chemical Dictionary, Eleven Edition, cover page, contents page, pp. 862-863, Van Nostrand Reinhold Company, Apr. 1987.

IUPAC Compendium of Chemical Terminology, 2nd Ed. 1997, pp. 1-1670.

Janzen, et al., "Diagnosing Long-Chain Branching in Polyethylene," Journal of Mol. Struct., 485/486, 1999, pp. 569-584.

Joseph, et al., "Products of the Initial Reduction of the Phillips Catalyst by Olefins", Journal of Catalysis 377 (2019) 550-564.

Kentaro et al., "Selective photo-oxidation of neat cyclohexane in the liquid phase over V2O5/Al2O3", Journal of Molecular Catalysis A: Chemical, vol. 208, No. 1-2, (Feb. 1, 2004-), pp. 299-306.

Kim, et.al., "Surface Structure and Reactivity of CrO3/SiO2 Catalysts," J. of Catalysis, vol. 136, 1992, p. 209-221. DOI:10.1016/0021-9517(92)90120-7.

Kissin, et al., "Chemistry of Olefin Polymerization Reactions with Chromium-Based Catalysts", Journal of Polymer Science: Part A: Polymer Chemostry, 2008, 46, 5330-5347.

Kohler, et al., "Infrared Spectroscopic Characterization of Chromium Carbonyl Species Formed by Ultraviolet Photoreduction of Silica-Supported Chromium(VI) in Carbon Monoxide," J. Phys. Chem. 1994, 98, pp. 4336-4342.

Kurek, et al, "Mesoporous Silica Supported Multiple Single-Site Catalysts and Polyethylene Reactor Blends with Tailor-Made Trimodal and Ultra-Broad Molecular Weight Distributions," Macromolecular Rapid Communications, vol. 31, No. 15, Jun. 22, 2010, pp. 1359-1363, DOI: 10.1002/marc.201000074.

Max P McDaniel: "Review of Phillips Chromium Catalyst for Ethytene Polymerization (Chapter 10)" In: "Handbook of Transition Metal Polymerization Catalysts", Aug. 31, 2010 (Aug. 31, 2010), Wiley, US, XP055562084, ISBN: 978-1-119-24213-0 pp. 291-446.

MAX P. McDaniel, "Chapter 3—Review of the Phillips Supported Chromium Catalyst and Its Commercial Use for Ethylene Polymerization", Advances in Catalysis, Academic Press, vol. 53, 2010, pp. 123-606. DOI: 10.1016/S0360-0564(10)53003-7.

McDaniel, et al., "The Activation of the Phillips Polymerization Catalyst; I. Influence of the Hydroxyl Population", Journal of Catalysis, vol. 82, No. 1, Jul. 1, 1983, pp. 98-109.

Milas, N .A., The hydroxylation of unsaturated substances III. The use of vanadium pentoxide and chromium trioxide as Catalysts of hydroxylation, The Journal of the American Chemical Society, vol. 58, No. 11, pp. 2342-2344 (Year: 1937).

Milas, N.A. et al., The hydroxylation of unsaturated substances IV. The catalytic hydroxylation of unsaturated hydrocarbons, The Journal of the American Chemical Society, vol. 59, No. 11, pp. 2345-2347 (Year: 1937).

Mino, et al., "Photoinduced Ethylene Polymerization on the CrVI/SiO2 Phillips Catalyst," J. Phys. Chem. C 2019, 123, 13 pp. 8145-8152.

Monwar, et.al., "Ethylene polymerization by hydrocarbon-reduced Cr/silica catalyst", Journal of Catalysis 394 (2021) 451-464. DOI 10.1016/j.jcat.2020.10.019.

Potter, et al., "Reduction of the Phillips Catalyst by Various Olefins: Stoichiometry, Thermochemistry, Reaction Products and Polymerization Activity", J. Catal. 344 (2016) 657-668.

Schwerdtfeger, E., et al., Reduction of Cr(VI) polymerization catalysts by non-olefinic hydrocarbons, Applied Catalysis A: General, 423-424, pp. 91-99 (Year: 2012).

Scott, et al. "Surface Organometallic Investigation of the Mechanism of Ethylene Polymerization by Silica-Supported Cr Catalysts", J. Chem. Eng. Sci. 2001, 56, 4155-4163.

Takenaka S et al., "Effect of alkali-metal ion addition to silica-supported molybdenum oxide on photocatalysis", Journal of the Chemical Society, Faraday Transactions, vol. 94, No. (Mar. 7, 1998), pp. 695-700. DOI: 10.1039/A707471I.

Tanaka et al., "Enhanced photocatalytic activity of quantum-confined tungsten trioxide nanoparticles in mesoporous silica", Chemical Communication, vol. 46, No. 29, (Jan. 1, 2010), p. 5286, DOI 10.1039/c0cc00540a.

Taylor, CE, et al. "New Development the Photocatalytic Conversion of Methane to Methanol", Catalysis Today , 55 (3): 259-267.

Thompson, et al. "'Sigma-Bond metathesis' for carbon-hydrogen bonds of hydrocarbons and Sc-R (R = H, alkyl, aryl) bonds of permethyiscandocene derivatives Evidence for noninvolvement of the pi system in electrophilic activation of aromatic and vinylic C—H bonds", J. Am. Chem. Soc. 1987, 109, 203-219.

Vaisman, E., et al., "A fluidized bed photoreactor exploiting a supported phocatalyst with adsorption pre-concentration capacity," Journal of Applied Electrochemistry, 35:675-681 (Year: 2005). DOI:10/1007/s10800-005-1389-1.

(56) References Cited

OTHER PUBLICATIONS

Vidal, et al. "Metathesis of Alkanes Catalyzed by Silica-Supported Transition Meal Hydrides", Science, v 276, issue 5309, Apr. 4, 1997, pp. 99-102. DOI: 10.1126/science.276.5309.99.

Vlasenko, VM, et al. "Formation of Methane in Methanol Synthesis on Zinc-Chromium Catalysts", Reaction Kinetics and Catalysis Letters, 6 (2): 195-200 1977.

Walker, GS, et. al. "Partial Oxidation of a Methane to Methanol—Comparison of Heterogeneous Catalyst and Homogeneous Gas-Phase Reactions", Catalysis Today, 21 (2-3): p. 519-526, 1994.

Weckhuysen et al., "Alkane dehydrogenation over supported chromium oxide catalysts," Catalysis Today 51 (1999) pp. 223-232.

Welch, et al., "The Activation of the Phillips Polymerization Catalyst; II. Actication By Reduction-Reoxidation", J Catalysis, vol. 82, No. 1, Jul. 1, 1983, pp. 110-117.

Wikipedia, Ultraviolet, Oct. 2019, p. 1-17 (Year: 2019).

Zhu et al., "Synthesis and Structural Characterization of M(PMe3)3(O2CR)2(OH2)H2 (M) Mo, W): Aqua-Hydride Complexes of Molybdenum and Tungsten", Inorg. Chem. 2005, 44, 9637-9639.

\* cited by examiner

METHANOL PRODUCTION FROM METHANE UTILIZING A SUPPORTED CHROMIUM CATALYST

REFERENCE TO RELATED APPLICATION

This application is a divisional application of U.S. patent application Ser. No. 18/494,846, filed on Oct. 26, 2023, now U.S. Pat. No. 12,134,591, which claims the benefit of and priority to U.S. Provisional Patent Application No. 63/381,580, filed on Oct. 31, 2022, the disclosures of which are incorporated herein by reference in their entirety.

FIELD OF THE INVENTION

The present disclosure generally relates to methods for converting methane into methanol, and more particularly, relates to performing such methods with chromium catalysts in a wet oxidizing atmosphere.

BACKGROUND OF THE INVENTION

Alcohol compounds, such as methanol, can be prepared by various synthesis techniques from alkanes, such as methane, but such techniques often require halogens or harsh reaction conditions. Alternative reaction schemes are therefore desirable. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

A first process described herein can be used to convert methane into methanol. This first process can comprise (i) contacting methane, water, and a supported chromium catalyst comprising chromium in a hexavalent oxidation state with a light beam at a wavelength in the UV-visible spectrum in an oxidizing atmosphere in a single reactor to form a reaction product comprising methanol, (ii) discharging a reactor effluent containing the reaction product from the single reactor, and (iii) separating methanol from the reaction product. The first process also can include a step of (iv) calcining (or activating) the supported chromium catalyst to regenerate at least a portion of the supported chromium catalyst.

A second process described herein also can be used to convert methane into methanol. This second process can comprise (a) contacting methane and a supported chromium catalyst comprising chromium in a hexavalent oxidation state with a light beam at a wavelength in the UV-visible spectrum, optionally in an oxidizing atmosphere, in a first reactor to form a form a reduced chromium catalyst, (b) contacting the reduced chromium catalyst with water, optionally in an oxidizing atmosphere, in a second reactor to form a reaction product comprising methanol, (c) discharging a reactor effluent containing the reaction product from the second reactor, and (d) separating methanol from the reaction product. The second process also can include a step of (e) calcining (or activating) the reduced chromium catalyst to regenerate at least a portion of the supported chromium catalyst.

Related production systems also are disclosed herein. A first methanol production system can comprise (I) a single fluidized bed reactor configured to produce a reaction mixture comprising methanol from methane and water in the presence of a supported chromium catalyst in an oxidizing atmosphere, wherein the reactor comprises a source of a light beam at a wavelength in the UV-visible spectrum, (II) a separations system configured to isolate methanol from a reactor effluent discharged from the reactor, and (III) a recycle system configured to convey unreacted methane, water, and oxygen/air back to the reactor. The first system also can include (IV) an activation vessel configured to regenerate at least a portion of the supported chromium catalyst.

A second methanol production system can comprise (A) a first fluidized bed reactor configured to produce a reduced chromium catalyst from methane in the presence of a supported chromium catalyst, optionally in an oxidizing atmosphere, wherein the reactor comprises a source of a light beam at a wavelength in the UV-visible spectrum, (B) a second fluidized bed reactor configured to produce a reaction mixture comprising methanol from the reduced chromium catalyst and water, optionally in an oxidizing atmosphere, (C) a separations system configured to isolate methanol from a reactor effluent discharged from the second reactor, and (D) a recycle system configured to convey unreacted methane, water, and oxygen/air back to the first fluidized bed reactor or the second fluidized bed reactor. The second system also can include (E) an activation vessel configured to regenerate at least a portion of the supported chromium catalyst.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description.

Figure 1:
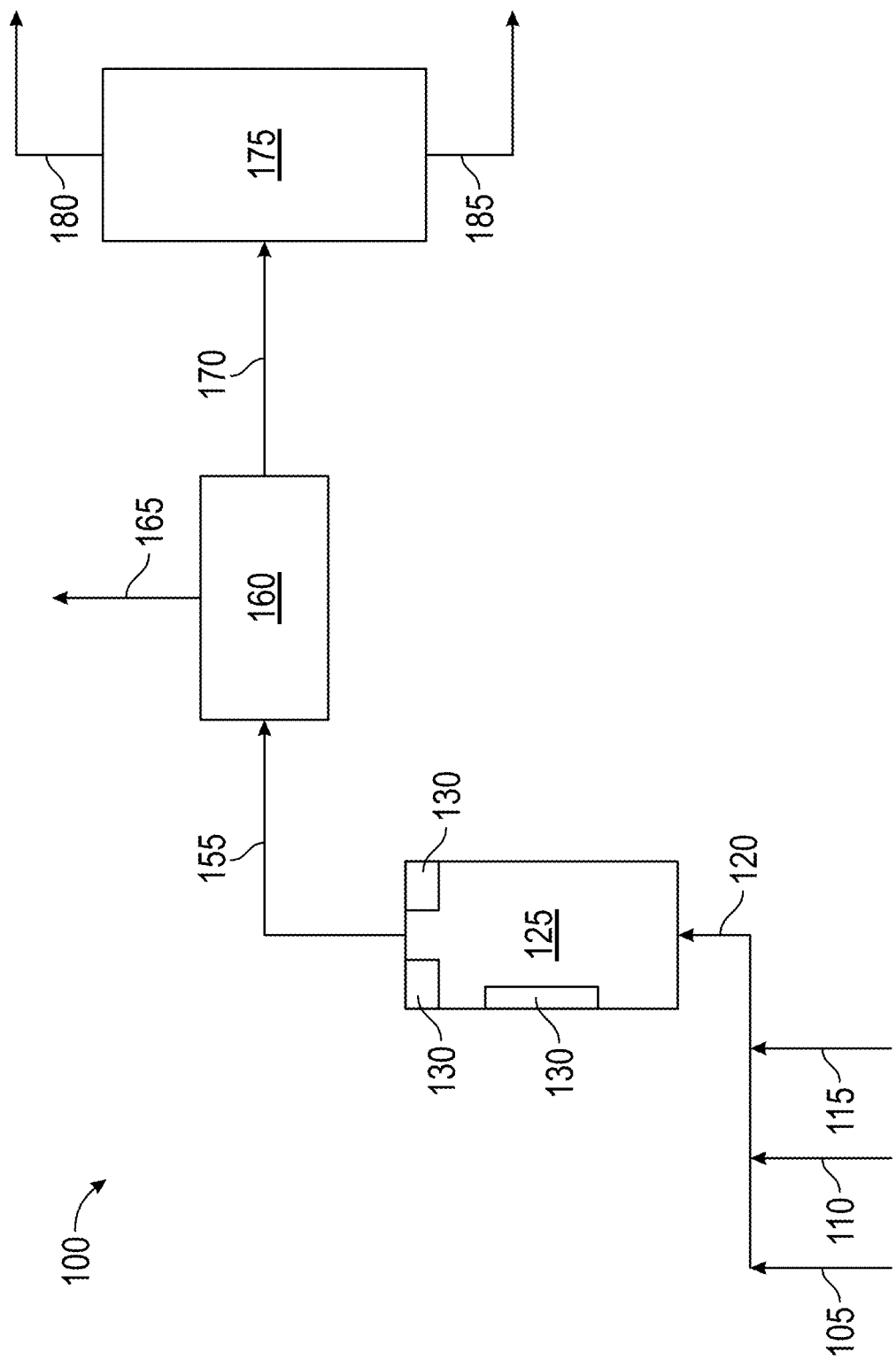
FIG. 1 illustrates a first methanol production system consistent with an aspect of the present disclosure.

While the inventions disclosed herein are susceptible to various modifications and alternative forms, only a few specific aspects have been shown by way of example in the drawings and described in detail below. The figures and detailed descriptions of these specific aspects are not intended to limit the breadth or scope of the inventive concepts or the appended claims in any manner. Rather, the figures and detailed descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the systems, compositions, processes, or methods described herein are contemplated with or without explicit description of the particular combination. Additionally, unless explicitly recited otherwise, any aspect or feature disclosed herein can be combined to describe inventive systems, compositions, processes, or methods consistent with the present disclosure.

Generally, groups of elements are indicated using the numbering scheme indicated in the version of the periodic table of elements published in *Chemical and Engineering News,* 63 (5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

"BET surface area" as used herein means the surface area as determined by the nitrogen adsorption Brunauer, Emmett, and Teller (BET) method according to ASTM D1993-91, and as described, for example, in Brunauer, S., Emmett, P. H., and Teller, E., "Adsorption of gases in multimolecular layers," J. Am. Chem. Soc., 60, 3, pp. 309-319.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. Likewise, the terms "a," "an," and "the" are intended to include plural alternatives, e.g., at least one, unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, by a disclosure that the supported chromium catalyst contains an amount of chromium in a range from 0.01 to 50 wt. %, the intent is to recite that the amount of chromium can be any amount in the range and, for example, can include any range or combination of ranges from 0.01 to 50 wt. %, such as from 0.01 to 10 wt. %, from 0.05 to 15 wt. %, from 0.1 to 5 wt. %, from 0.2 to 10 wt. %, from 0.5 to 30 wt. %, or from 1 to 10 wt. %, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

The present invention is generally directed to the conversion of methane into methanol in the presence of a supported chromium (VI) catalyst in both a wet and oxidizing atmosphere and with exposure to UV irradiation.

It was expected, due to the well-known ability of oxygen to stop polymerization on chromium-based catalysts, that performing this methane to methanol synthesis in an oxidizing atmosphere would result in minimal to no formation of the desired methanol. However, instead, significant increases in the molar yield of methanol (based on the chromium present in the catalyst) can result from the presence of oxygen.

Also surprisingly, the presence of water did not halt the reduction reaction involving chromium and methane, and the chromium catalyst can be both hydrolyzed and re-oxidized in the presence of both water (e.g., steam) and oxygen (e.g., air). Thus, while not wishing to be bound by theory, a methane derivative binds to chromium during the UV triggered reduction of hexavalent chromium, water displaces the methane derivative from the catalyst as methanol, and oxygen re-oxidizes the chromium catalyst to a hexavalent oxidation state in order to complete the reaction cycle.

Processes for Converting Methane into Methanol

Disclosed herein are processes for converting methane into methanol. A first process can comprise (or consist essentially of, or consist of) (i) contacting methane, water, and a supported chromium catalyst comprising chromium in a hexavalent oxidation state with a light beam at a wavelength in the UV-visible spectrum in an oxidizing atmosphere in a single reactor to form a reaction product comprising methanol, (ii) discharging a reactor effluent containing the reaction product from the single reactor, and (iii) separating methanol from the reaction product. The first process also can include a step of (iv) calcining (or activating) the supported chromium catalyst to regenerate at least a portion of the supported chromium catalyst.

A second process described herein also can be used to convert methane into methanol, and the second process can comprise (or consist essentially of, or consist of) (a) contacting methane and a supported chromium catalyst comprising chromium in a hexavalent oxidation state with a light beam at a wavelength in the UV-visible spectrum, optionally in an oxidizing atmosphere, in a first reactor to form a form a reduced chromium catalyst, (b) contacting the reduced chromium catalyst with water, optionally in an oxidizing atmosphere, in a second reactor to form a reaction product comprising methanol, (c) discharging a reactor effluent containing the reaction product from the second reactor, and (d) separating methanol from the reaction product. While not wishing to be bound by theory, it is believed that in step (a), at least a portion of the chromium on the reduced chromium catalyst can have at least one bonding site with a methoxy group, which upon hydrolysis in step (b), can release methanol. The reduced chromium catalyst can have an average oxidation state less than that of the parent supported chromium catalyst. The second process also can include a step of (e) calcining (or activating) the reduced chromium catalyst to regenerate at least a portion of the supported chromium catalyst.

Generally, the features of the first process and the second process (e.g., the supported chromium catalyst, the reduced chromium catalyst, the light beam, the oxidizing atmosphere, and the conditions under which the contacting steps and the separating steps are conducted, among others) are independently described herein and these features can be combined in any combination to further describe the disclosed processes to produce methanol from methane. Moreover, additional process steps can be performed before, during, and/or after any of the steps in any of the processes disclosed herein, and can be utilized without limitation and in any combination to further describe these processes, unless stated otherwise. Further, any methanol products produced in accordance with the disclosed processes are within the scope of this disclosure and are encompassed herein.

In the first and second processes, any suitable temperature and pressure conditions can be used, although highly elevated temperatures (e.g., above 300° C.) are not required due to the irradiation with the light beam at the wavelength in the UV-visible spectrum. In certain aspects, step (i) and step (a) and step (b) are conducted, independently, at a temperature of less than or equal to 300° C., less than or equal to 200° C., less than or equal to 100° C., from 100° C. to 300° C., from −100° C. to 100° C., from 0° C. to 100° C., from 20° C. to 250° C., from 20° C. to 150° C., or from 10° C. to 40° C., and the like. These temperature ranges also are meant to encompass circumstances where step (i) and step (a) and step (b) are performed, independently, at a series of different temperatures, instead of at a single fixed temperature, falling within the respective temperature ranges, wherein at least one temperature is within the recited ranges. Likewise, the pressure utilized during step (i) and step (a) and step (b) is not particularly limited, but generally falls within a range, independently, of from 5 to 1000 psig (34 to 6895 kPa), from 10 to 200 psig (69 kPa to 1379 kPa), or from 20 to 250 psig (138 kPa to 1724 kPa), and the like. These pressure ranges also are meant to encompass circumstances where step (i) and step (a) and step (b) are performed, independently, at a series of different pressures, instead of at a single fixed pressure, falling within the respective pressure ranges, wherein at least one pressure is within the recited ranges.

Often, the first and second processes for converting methane into methanol can be a flow process and/or a continuous process. In such circumstances, the methane-supported chromium catalyst contact time (or reaction time) can be expressed in terms of weight hourly space velocity (WHSV)—the ratio of the weight of the methane which comes in contact with a given weight of the supported chromium catalyst per unit time (measured in units of g/g/hr, or $hr^{-1}$).

While not limited thereto, the WHSV employed for step (i) of the first process and step (a) of the second process can have a minimum value of 0.01 $hr^{-1}$, 0.02 $hr^{-1}$, 0.05 $hr^{-1}$, 0.1 $hr^{-1}$, 0.25 $hr^{-1}$, or 0.5 $hr^{-1}$; or alternatively, a maximum value of 500 $hr^{-1}$, 400 $hr^{-1}$, 300 $hr^{-1}$, 100 $hr^{-1}$, 50 $hr^{-1}$, 10 $hr^{-1}$, 5 $hr^{-1}$, 2 $hr^{-1}$, or 1 $hr^{-1}$. Generally, the WHSV can be in a range from any minimum WHSV disclosed herein to any maximum WHSV disclosed herein. In a non-limiting aspect, the WHSV can be in a range from 0.01 $hr^{-1}$ to 500 $hr^{-1}$; alternatively, from 0.01 $hr^{-1}$ to 10 $hr^{-1}$; alternatively, from 0.01 $hr^{-1}$ to 1 $hr^{-1}$; alternatively, from 0.02 $hr^{-1}$ to 400 $hr^{-1}$; alternatively, from 0.02 $hr^{-1}$ to 50 $hr^{-1}$; alternatively, from 0.05 hr-1 to 300 $hr^{-1}$; alternatively, from 0.05 $hr^{-1}$ to 5 $hr^{-1}$; alternatively, from 0.1 $hr^{-1}$ to 400 $hr^{-1}$; alternatively, from 0.1 $hr^{-1}$ to 10 $hr^{-1}$; alternatively, from 0.25 $hr^{-1}$ to 2 $hr^{-1}$; alternatively, from 0.5 $hr^{-1}$ to 400 $hr^{-1}$; alternatively, from 0.5 $hr^{-1}$ to 5 $hr^{-1}$; or alternatively, from 0.5 $hr^{-1}$ to 3 $hr^{-1}$. Other WHSV ranges are readily apparent from this disclosure.

The supported chromium catalyst and methane can be continuously subjected to irradiation (for the entirety of the exposure time), or the irradiation can be pulsed (such that the total of the pulses equates to the exposure time, e.g., sixty 1-sec pulses equates to a 60-sec exposure time). Combinations of periods of continuous irradiation and pulsed irradiation can be utilized, if desired.

In the disclosed processes, irradiation of the supported chromium catalyst with a light beam in the UV-visible spectrum, in the presence of methane, can utilize a wide range of wavelengths, light sources, and intensities, as long as these wavelengths, light sources, and intensities are sufficient to convert methane into methanol. In certain aspects, for instance, the light can be derived from any suitable source, such as from a fluorescent white light, an LED diode, and/or a UV lamp. The distance from these light sources can be varied as needed (e.g., minimized) to increase the effectiveness of the irradiation.

While not being limited thereto, the single reactor in the first process and the first reactor in the second process can have one or more immersion lamps as a source of the light beam attached to the top, or attached to the bottom, or attached to the wall, or positioned in the wall of the respective reactor, or any combination of these locations. Additionally or alternatively, the single reactor in the first process and the first reactor in the second process can have one or more internal light sources of the light beam (e.g., immersion lamps) in the interior of the respective reactor. The internal light sources can enter the respective reactor through a port (one or more) positioned at a side/wall of the reactor.

The wavelength of the light can be any in the range of UV-visible light. In certain aspects, the wavelength of the light beam can be a single wavelength, or more than one wavelength, such as a range of wavelengths. For instance, the wavelength of the light beam can be a range of wavelengths spanning at least 5 nm, at least 10 nm, at least 25 nm, or at least 50 nm, for instance, wavelength ranges spanning 5 to 50 nm, or spanning 5 to 25 nm. In one aspect, the wavelength of the light beam can comprise a single wavelength or a range of wavelengths in the UV spectrum, in the visible spectrum (from 380 nm to 780 nm), or both. In another aspect, the wavelength of the light beam can comprise a single wavelength or a range of wavelengths in the 200 nm to 750 nm range. Yet, in another aspect, the wavelength of the light beam can comprise a single wavelength or a range of wavelengths in the 300 to 750 nm range, the 350 nm to 650 nm range, the 300 nm to 500 nm range, the 350 to 450 nm range, the 300 nm to 400 nm range, the 385 to 400 nm range, or the 395 to 405 nm range.

In other aspects, the wavelength of the light beam can comprise a single wavelength or a range of wavelengths below 600 nm, below 525 nm, or below 500 nm; additionally or alternatively, above 300 nm, above 350 nm, above 400 nm, or above 450 nm. Beneficially, blue light and UV light sources are typically more effective, thus the wavelength of the light beam can comprise a single wavelength or a range of wavelengths below 475 nm; alternatively, below 450 nm; alternatively, below 430 nm; or alternatively, below 420 nm; and additionally or alternatively, above 350 nm; alternatively, above 370 nm; alternatively, above 380 nm; or alternatively, above 400 nm.

The light beam used in step (i) or step (a) also can be characterized by its intensity (e.g., the total amount of light emitted from a source). In certain aspects, the light beam (or light beams) can have an intensity of at least 500 lumens, at least 1,000 lumens, at least 2,000 lumens at least 5,000 lumens, at least 10,000 lumens, at least 20,000 lumens, at least 50,000 lumens, or at least 100,000 lumens. Thus, there may not be an upper limit on the intensity of the light source. Alternatively, the light beam (or light beams) can have an intensity in a range from 50 to 50,000 lumens, from 50 to 10,000 lumens, from 100 to 5,000 lumens, or from 500 to 2,000 lumens. Additionally, the light beam(s) can be characterized by the amount of light reaching the methane reactant and supported chromium catalyst, i.e., the flux. In certain aspects, the methane reactant and the supported chromium catalyst can be irradiated by at least 100 lux, at least 500 lux, at least 1000 lux, at least 2000 lux, at least 5000 lux, at least 10,000 lux, at least 20,000 lux, at least 50,000 lux, at least 100,000 lux, or in a range from 10,000 to 1,000,000 lux, from 10,000 to 250,000 lux, from 10,000 to 100,000 lux, from 20,000 to 200,000 lux, from 20,000 to 100,000 lux, from 50,000 to 500,000 lux, or from 50,000 to 200,000 lux. Additionally or alternatively, in certain aspects, the methane reactant and the supported chromium catalyst can be irradiated with a light beam (or light beams) from a light source (or light sources) having a power of at least 50 watts, at least 100 watts, at least 1,000 watts, at least 10,000 watts, or at least 100,000 watts. The light power can depend upon the size of the reactor, the number of bulbs or light sources utilized, the residence time and WHSV, among other variables.

Any suitable reactor or vessel can be used in the first process and the second process, non-limiting examples of which can include a flow reactor, a continuous reactor, a packed bed reactor, a fluidized bed reactor, and a stirred tank reactor, including more than one reactor in series or in parallel, and including any combination of reactor types and arrangements. In a particular aspect contemplated herein, step (i) of the first process and step (a) of the second process utilize a fluidized bed reactor, therefore, step (i) and step (a) comprise contacting methane with a fluidized bed of the supported chromium catalyst while irradiating (methane is in the gas phase during step (i) and step (a)).

In one aspect, the single reactor in the first process is a fluidized bed reactor, while in another aspect, the first reactor in the second process is a fluidized bed reactor, and in yet another aspect, both the single reactor and the first reactor are fluidized bed reactors. There can be a reactor configured in parallel to the single reactor and/or the first reactor, and this can be a back-up reactor that is substantially the same as the respective single reactor and first reactor described herein. The back-up reactor can be used when the single reactor and/or the first reactor is out of service for maintenance, for catalyst regeneration, and so forth. Alternatively, the back-up reactor can be used simultaneously with the single reactor and/or the first reactor to allow for reduced production losses when a reactor is out of service for maintenance, for catalyst regeneration, and so forth. The back-up reactor generally is positioned in parallel, such that swapping from one to other is relatively easy. Likewise, in the second process, the second reactor also can be a fluidized bed reactor, and there can be a back-up reactor for the second reactor, generally configured in parallel.

The linear velocity of the fluidizing gas stream in the respective fluidized bed reactor is not particularly limited. In one aspect, for instance, the linear velocity can range from 0.03 to 2 ft/sec. In another aspect, the linear velocity can range from 0.1 to 1.5 ft/sec. In yet another aspect, the linear velocity can range from 0.2 to 1.5 ft/sec or from 0.5 to 1.5 ft/sec. In still another aspect, the linear velocity can range from 0.7 to 1.2 ft/sec.

The average contact time of the supported chromium catalyst with methane in the fluidized bed reactor can be quantified based on the linear velocity of the fluidizing gas stream and the fluidized bed height (for a single pass). Generally, the average contact time (for a single pass) can range from 1 sec to 300 sec, from 3 sec to 150 sec, from 3 sec to 60 sec, from 5 sec to 90 sec, from 5 sec to 45 sec, from 10 sec to 150 sec, or from 10 sec to 30 sec, and the like, although not limited thereto.

In the first process and the second process, the relative amount (or concentration) of the methane reactant to the amount of chromium (of the supported chromium catalyst) can alter the efficacy of the methanol production process. In certain aspects, the molar ratio of methane to the chromium (of the supported chromium catalyst) can be at least 0.25:1, at least 0.5:1, at least 1:1, at least 10:1, at least 100:1, at least 1000:1, or at least 10,000:1. Thus, a large excess of methane can be used, and there is no particular limit as to the maximum amount of methane, relative to chromium, that can be used in the respective reactor (e.g., fluidized bed reactor).

The oxidizing atmosphere in the first process and the second process is not particular limited. Typical materials used to create the oxidizing atmosphere include, but are not limited to, oxygen, air, a mixture of air and an inert gas (such as nitrogen), a mixture of oxygen and an inert gas, NO, $NO_2$, $N_2O$, ozone, a halide oxide, $H_2O_2$, an organic peroxide, and the like, as well as combinations thereof. For convenience, air is often used, and thus air can be injected into the respective reactor(s) in the first process and the second process to result in the oxidizing atmosphere. As it pertains to the second process, the oxidizing atmosphere can be present in the first reactor in one aspect of the invention, while in another aspect, the oxidizing atmosphere can be present in the second reactor, and in yet another aspect, the oxidizing atmosphere can be present in both the first reactor and the second reactor.

The molar ratio of molecular oxygen or other oxidizing agent to chromium (of the supported chromium catalyst or of the reduced chromium catalyst, in the single reactor, the first reactor, and/or the second reactor, as the context requires for the respective process) is not particularly limited, but often can be at least 0.25:1, at least 0.5:1, at least 1:1, at least 2:1, at least 10:1, at least 100:1, at least 1000:1, or at least 10,000:1. Thus, a large excess of the molecular oxygen or other oxidizing agent can be used, and there is no particular limit as to the maximum amount of molecular oxygen or other oxidizing agent in the oxidizing atmosphere in the respective reactor (e.g., fluidized bed reactor). For instance, a large molar excess of air can be used in the first and second processes.

Likewise, the molar ratio of water to chromium (of the supported chromium catalyst or the reduced chromium catalyst, in the single reactor or the second reactor, as the context requires for the respective process) is not particularly limited, but often can be at least 0.25:1, at least 0.5:1, at least 1:1, at least 5:1, at least 10:1, at least 100:1, at least 1000:1, or at least 10,000:1. Hence, a large excess of water can be used in the first and second processes. Water can be added via steam injection into the single reactor in step (i) of the first process and into the second reactor in step (b) of the second process, or water can be added via water vapor injection into the single reactor and the second reactor, as well as other suitable methodologies (e.g., with a fluidizing gas medium, such as air).

In contrast, the relative amounts of methane, oxygen/air, and water are often in more confined ranges. For example, and while not always limited thereto, the minimum water:methane molar ratio can be 1:5, 1:3, 1:2, 1:1.5, or 1:1.2, and additionally or alternatively, the maximum water:methane molar ratio can be 5:1, 3:1, 2:1, 1.5:1, or 1.2:1. In an aspect, the water:methane molar ratio in the respective reactor can be in a range from any minimum molar ratio disclosed herein to any maximum molar ratio disclosed herein. In some non-limiting aspects, the molar ratio therefore can be in a range from 1:5 to 5:1, from 1:3 to 3:1, from 1:2 to 2:1, from 1:1.5 to 1.5:1, or from 1:1.2 to 1.2:1, and the like. Additionally, in some aspects, it can be beneficial to limit the excess amount of water present, since excess water may react with silica supports to form silanols. As those skilled in the art would readily recognize, the water:methane molar ratio can change as the methane is reacted and/or as methanol is formed.

Similarly, and while not always limited thereto, the minimum oxygen ($O_2$):methane molar ratio can be 0.05:1, 0.1:1, 0.2:1, 0.3:1, or 0.4:1, and additionally or alternatively, the maximum oxygen ($O_2$):methane molar ratio can be 5:1, 3:1, 1:1, or 0.6:1. In an aspect, the oxygen ($O_2$):methane molar ratio in the respective reactor can be in a range from any minimum molar ratio disclosed herein to any maximum molar ratio disclosed herein. In some non-limiting aspects, the molar ratio therefore can be in a range from 0.1:1 to 5:1, from 0.2:1 to 3:1, from 0.1:1 to 1:1, from 0.3:1 to 1:1, or from 0.4:1 to 0.6:1, and the like. Additionally, in some aspects, it can be beneficial for oxygen to be the limiting reactant as compared to methane. As those skilled in the art would readily recognize, the oxygen ($O_2$):methane molar ratio can change as the methane is reacted and/or as methanol is formed. Note that methane can be fed to the respective reactor in the same gas inlet as oxygen in a mixture, or separate feed streams can be used.

The processes described herein result in an unexpectedly high conversion of methane and/or yield to methanol. In one aspect, the minimum conversion of methane (or yield to methanol based on the methane reactant) can be at least 2 wt. %, at least 5 wt. %, at least 10 wt. %, at least 15 wt. %, or at least 25 wt. %.

Additionally, the maximum conversion (or yield) can be 50 wt. %, 70 wt. %, 80 wt. %, 90 wt. %, 95 wt. %, or 99 wt. %, and can approach 100% conversion of the methane reactant (or yield of methanol). Generally, the conversion (or yield) can be in a range from any minimum conversion (or yield) disclosed herein to any maximum conversion (or yield) disclosed herein. Non-limiting ranges of conversion (or yield) can include from 5 wt. % to 99 wt. %, from 10 wt. % to 95 wt. %, or from 15 wt. % to 70 wt. %. For conversion, the percentages are the amount of the methane reactant converted based on the initial amount of methane. The yield values are weight percentages, and are based on the weight of the methanol produced to the weight of methane reactant. In some aspects, these conversions (or yields) can be achieved in a batch process, while in other aspects, these conversions (or yields) can be achieved in a flow or continuous process, such as, for example, a single pass or multiple passes through a reactor (e.g., a fluidized bed reactor). Often, the conversion and yield can be manipulated by varying the ratio of methane feed to the amount of chromium (VI), the amount of oxygen in the oxidizing atmosphere, and by varying other reaction conditions such as time, temperature, and irradiation.

Also unexpectedly, continuous flow processes for producing methanol in accordance with this invention have unexpectedly high single pass conversions of the methane reactant (or single pass yields to the desired methanol product). In one aspect, the minimum single pass conversion (or yield) can be at least 2 wt. %, at least 5 wt. %, at least 10 wt. %, at least 15 wt. %, or at least 25 wt. %. Additionally, the maximum single pass conversion (or yield) can be 50 wt. %, 70 wt. %, 80 wt. %, 90 wt. %, 95 wt. %, or 99 wt. %, and can approach 100% conversion of the methane reactant (or yield of methanol), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from 5 wt. % to 99 wt. %, from 10 wt. % to 95 wt. %, or from 15 wt. % to 70 wt. %. In a fluidized bed reactor, it may be necessary to maintain a relatively high methane flow, along with other gasses, to keep the bed fluidized. In such circumstances, lower single pass conversions (or single pass yields) may result, such as from 1 to 50 wt. %, from 1 to 25 wt. %, from 1 to 15 wt. %, from 2 to 20 wt. %, or from 5 to 25 wt. %.

In the first and second processes, the yield of methanol also can be characterized based on the amount of chromium (VI) (of the supported chromium catalyst). For instance, the molar ratio (molar yield) of methanol based on the moles of chromium (VI) can be at least 0.01 moles, at least 0.025 moles, at least 0.05 moles, at least 0.1 moles, at least 0.25 moles, or at least 0.5 moles of methanol per mole of Cr(VI). While not limited thereto, the yield in moles of methanol per mole of Cr(VI) often can be up to 100 moles, up to 80 moles, up to 50 moles, up to 30 moles, up to 20 moles, up to 15 moles, up to 10 moles, up to 5 moles, up to 5 moles, up to 3 moles, or up to 1 mole of the methanol. A particularly desirable target for the moles of methanol produced per mole of chromium (VI) of the supported chromium catalyst is at least 2:1 (2 moles of methanol per 1 mole of Cr before regeneration).

Referring now to step (ii) of the first process, in which the reactor effluent containing the reaction product is discharged from the single reactor, and step (c) of the second process, in which the reactor effluent containing the reaction product is discharged from the second reactor, the reactor effluent typically contains methanol, unreacted methane, reaction by-products, steam/water, and oxygen (air). The reaction product typically contains methanol, reaction by-products (e.g., formic acid or formaldehyde and/or secondary addition products of formaldehyde), and water.

In an aspect, the first process and second process can further comprise a step of separating the reaction product from the reactor effluent using any suitable technique, an example of which is condensing. Thus, at least a portion of the methanol, reaction by-product, and water can be separated from the reactor effluent and gaseous materials, such as methane and oxygen (air). Optionally, unreacted methane and/or oxygen (air) from the reactor effluent can be recycled back to the single reactor in the first process and the first reactor in the second process.

Referring now to step (iii) of the first process and step (d) of the second process, methane is separated from the reaction product. This can be accomplished using any suitable technique, which can include but is not limited to, extraction, filtration, evaporation, or distillation, as well as combinations of two or more of these techniques. In particular aspects of this invention, the isolating or separating step utilizes distillation at any suitable temperature and pressure (one or more than one distillation column can be used) to separate methanol from the reaction by-products (e.g., formic acid, water, formaldehyde and its addition products).

Although it is expected the amount of formic acid will be minimal, the first and second processes for converting methane into methanol can further comprise a step of neutralizing formic acid or converting formic acid to a non-corrosive compound, if desired. For instance, formic acid can be neutralized with a base, of which NaOH and $NaCO_3$ are non-limiting examples. Formic acid can be converted to a non-corrosive compound—for example, an ester such as methyl formate-via the use of a basic catalyst.

Referring now to the chromium catalyst, after hydrolyzing to release methanol, the first and second processes can further comprise a step of separating at least a portion (and in some cases, all) of the supported chromium catalyst (or the reduced chromium catalyst) from the reaction product. Any suitable technique(s) can be used.

If desired, the first and second processes disclosed herein can further comprise a step of calcining/activating the supported chromium catalyst (or the reduced chromium catalyst) to regenerate at least a portion (and in some cases, all) of the supported chromium catalyst comprising chromium in a hexavalent oxidation state. Any suitable calcining/activating conditions can be used, for instance, subjecting the supported chromium catalyst or the reduced chromium catalyst to an oxidizing atmosphere at any suitable peak temperature and time conditions, such as a peak temperature from 300° C. to 1000° C., from 500° C. to 900° C., or from 350° C. to 600° C., for a time period of from 1 min to 24 hr, from 1 hr to 12 hr, or from 30 min to 8 hr, or from 1 hr to 3 hr.

The calcining/activating step can be conducted using any suitable technique and equipment, whether batch or continuous. For instance, the calcining/activating step can be performed in a belt calciner or, alternatively, a rotary calciner. In some aspects, the calcining/activating step can be performed in a batch or continuous calcination vessel comprising a fluidized bed. As would be recognized by those of skill in the art, other suitable techniques and equipment can be employed for the calcining/activating step, and such techniques and equipment are encompassed herein.

Chromium Catalysts

Generally, the first process and the second process are applicable to the reduction of any hexavalent chromium catalyst, and are not limited to the reduction of any particular type of supported chromium catalyst comprising chromium in a hexavalent oxidation state. Thus, supported chromium catalysts contemplated herein encompass those prepared by contacting a support with a chromium-containing compound-representative and non-limiting examples of the chromium-compound compound include chromium (III) acetate, basic chromium (III) acetate, chromium (III) acetylacetonate, $Cr_2(SO_4)_3$, $Cr(NO_3)_3$, and $CrO_3$—and calcining in an oxidizing atmosphere to form a supported chromium catalyst. In these aspects, chromium can be impregnated during, or prior to, the calcination step, which can be conducted at a variety of temperatures and time periods, and can be generally selected to convert all or a portion of the chromium to hexavalent chromium. The subsequent methane-contacting steps with irradiation disclosed herein can comprise reducing at least a portion of the hexavalent chromium species to a reduced oxidation state—for instance, Cr (II) and/or Cr (III) and/or Cr (IV) and/or Cr (V) species, any of which may be present on the reduced chromium catalyst.

Any suitable chromium-containing compound (or chromium precursor) can be used as a chromium component to prepare the supported chromium catalyst. Illustrative and non-limiting examples of chromium (II) compounds can include chromium (II) acetate, chromium (II) chloride, chromium (II) bromide, chromium (II) iodide, chromium (II) sulfate, and the like, as well as combinations thereof. Likewise, illustrative and non-limiting examples of chromium (III) compounds can include a chromium (III) carboxylate, a chromium (III) naphthenate, a chromium (III) halide, chromium (III) sulfate, chromium (III) nitrate, a chromium (III) dionate, and the like, as well as combinations thereof. In some aspects, the chromium-containing compound can comprise chromium (III) acetate, chromium (III) acetylacetonate, chromium (III) chloride, chromium (III) bromide, chromium (III) sulfate, chromium (III) nitrate, and the like, as well as combinations thereof.

While not required, it can sometimes be beneficial for the chromium-containing compound to be soluble in a hydrocarbon solvent or other organic solvent (alcohols, ketones, etc.) during preparation of the supported chromium catalyst. In such situations, the chromium-containing compound can comprise tertiary butyl chromate, a diarene chromium (0) compound, bis-cyclopentadienyl chromium (II), chromium (III) acetylacetonate, chromium acetate, and the like, or any combination thereof. Similarly, and not required, it can be beneficial for the chromium-containing compound to be soluble in water during preparation of the supported chromium catalyst. In such situations, the chromium-containing compound can comprise chromium trioxide, chromium acetate, chromium nitrate, and the like, or any combination thereof.

Other examples of chromium-containing compounds include sodium, potassium, or ammonium chromate or dichromate, which is unexpected, because such alkali metal chromates are not usually acceptable for use in polymerization catalysts because of low activity and sintering of the solid support. Thus, the chromium precursor can comprise a chromate compound, e.g., potassium chromate, sodium chromate, ammonium chromate, potassium dichromate, sodium dichromate, ammonium dichromate, and the like, as well as any combination thereof. Since chromium in already in the hexavalent state for these chromate compounds, heat treatment options other than traditional calcining in an oxidizing atmosphere can be used, such as low temperatures (and even an inert atmosphere) to dry or remove excess water/moisture prior to exposing the supported chromium catalyst to light irradiation.

Referring now to the first process and the second process, various solid supports can be used for the supported chromium catalyst (or the reduced chromium catalyst), such as conventional solid oxides and zeolites. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11th Ed., John Wiley & Sons, 1995; Cotton, F. A., Wilkinson, G., Murillo, C. A., and Bochmann, M., Advanced Inorganic Chemistry, 6th Ed., Wiley-Interscience, 1999). For example, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr. Illustrative examples of solid oxide materials or compounds that can be used as solid support can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as silica, alumina, or titania, "mixed oxide" compounds thereof such as silica-titania, and combinations or mixtures of more than one solid oxide material. Mixed oxides such as silica-titania can be single or multiple chemical phases with more than one metal combined with oxygen to form the solid oxide. Examples of mixed oxides that can be used as solid oxide include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. In some aspects, the solid support can comprise silica, silica-alumina, silica-coated alumina, silica-titania, silica-titania-magnesia, silica-zirconia, silica-magnesia, silica-boria, aluminophosphate-silica, and the like, or any combination thereof. Silica-coated aluminas are encompassed herein; such oxide materials are described in, for example, U.S. Pat. Nos. 7,884,163 and 9,023,959.

The percentage of each oxide in a mixed oxide can vary depending upon the respective oxide materials. As an example, a silica-alumina (or silica-coated alumina) typically has an alumina content from 5 wt. % to 95 wt. %. According to one aspect, the alumina content of the silica-alumina (or silica-coated alumina) can be from 5 wt. % alumina 50 wt. % alumina, or from 8 wt. % to 30 wt. % alumina. In another aspect, high alumina content silica-aluminas (or silica-coated aluminas) can be employed, in which the alumina content of these materials typically ranges from 60 wt. % alumina to 90 wt. % alumina, or from 65 wt. % alumina to 80 wt. % alumina.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, thoria, stania, zirconia, magnesia, boria, zinc oxide, a mixed oxide thereof, or any mixture thereof. In yet another aspect, the solid support can comprise silica, alumina, titania, or a combination thereof; alternatively, silica; alternatively, alumina; alternatively, titania; alternatively, zirconia; alternatively, magnesia; alternatively, boria; or alternatively, zinc oxide. In still another aspect, the solid oxide can comprise silica, alumina, silica-alumina, silica-coated alumina, aluminum phosphate, aluminophosphate, heteropolytungstate, titania, zirconia, magnesia, boria, zinc oxide, silica-titania, silica-yttria, silica-zirconia, alumina-titania, alumina-zirconia, zinc-aluminate, alumina-boria, silica-boria, aluminophosphate-silica, titania-zirconia, and the like, or any combination thereof.

Consistent with certain aspects of this invention, the supported chromium catalyst (or the reduced chromium catalyst) can comprise a chemically-treated solid oxide as the support, and where the chemically-treated solid oxide comprises a solid oxide (any solid oxide disclosed herein) treated with an electron-withdrawing anion (any electron withdrawing anion disclosed herein). The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed.

It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The chemically-treated solid oxide generally can contain from 1 wt. % to 30 wt. % of the electron-withdrawing anion, based on the weight of the chemically-treated solid oxide. In particular aspects provided herein, the chemically-treated solid oxide can contain from 1 to 20 wt. %, from 2 wt. % to 20 wt. %, from 3 wt. % to 20 wt. %, from 2 wt. % to 15 wt. %, from 1 wt. % to 10 wt. %, from 2 wt. % to 10 wt. %, from 3 wt. % to 10 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof.

In another aspect, the chemically-treated solid oxide employed in the supported chromium catalyst (or the reduced chromium catalyst) and the processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. Additional information on chemically-treated solid oxides can be found in, for instance, U.S. Pat. Nos. 7,294,599, 7,601,665, 7,884,163, 8,309,485, 8,623,973, and 8,703,886.

Representative examples of supported chromium catalysts and reduced chromium catalysts (in which a solid oxide is the support) include, but are not limited to, chromium/silica, chromium/silica-titania, chromium/silica-zirconia, chromium/silica-titania-magnesia, chromium/silica-alumina, chromium/silica-coated alumina, chromium/aluminophosphate, chromium/alumina, chromium/alumina borate, and the like, or any combination thereof. In one aspect, for instance, the supported chromium catalyst (or the reduced chromium catalyst) can comprise chromium/silica, while in another aspect, the supported chromium catalyst (or the reduced chromium catalyst) can comprise chromium/silica-titania, and in yet another aspect, the supported chromium catalyst (or the reduced chromium catalyst) can comprise chromium/silica-alumina and/or chromium/silica-coated alumina, and in still another aspect, the supported chromium catalyst (or the reduced chromium catalyst) can comprise chromium/alumina. It can be advantageous to use a support that allows high conversion to hexavalent chromium, one example of which is alumina, thus chromium/alumina can be suitably used as the supported chromium catalyst.

In circumstances in which the supported chromium catalyst (or the reduced chromium catalyst) comprises chromium/silica-titania (or chromium/silica-zirconia), any suitable amount of titanium (or zirconium) can be present, including from 0.1 to 20 wt. %, from 0.5 to 15 wt. %, from 1 to 10 wt. %, or from 1 to 6 wt. % titanium (or zirconium), based on the total weight of the respective catalyst.

Representative examples of supported chromium catalysts and reduced chromium catalysts (in which a chemically-treated solid oxide is the support) include, but are not limited to, chromium/sulfated alumina, chromium/fluorided alumina, chromium/fluorided silica-alumina, chromium/fluorided silica-coated alumina, and the like, as well as combinations thereof. Such chemically-treated supports often have lower hexavalent chromium conversion, thus an untreated solid oxide may be used instead as the support for chromium.

Consistent with certain aspects of this invention, the supported chromium catalyst (or the reduced chromium catalyst) can comprise a zeolite as the support, i.e., a chromium supported zeolite. Any suitable zeolite can be used, for instance, large pore and medium pore zeolites. Large pore zeolites often have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often have average pore diameters in a range of from about 5 Å to about 7 Å. Combinations of zeolitic supports can be used.

Additional representative examples of zeolites that can be used include, for instance, a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, and the like, or any combination thereof.

In the supported chromium catalyst (or the reduced chromium catalyst), the zeolite can be bound with a support matrix (or binder), non-limiting examples of which can include silica, alumina, magnesia, boria, titania, zirconia, various clays, and the like, including mixed oxides thereof, as well as mixtures thereof. For example, the supported chromium catalyst (or the reduced chromium catalyst) can comprise a binder comprising alumina, silica, a mixed oxide thereof, or a mixture thereof. The zeolite can be bound with the binder using any method known in the art. While not being limited thereto, the supported chromium catalyst (or the reduced chromium catalyst) can comprise a zeolite and from 3 wt. % to 35 wt. % binder; alternatively, from 5 wt. % to 30 wt. % binder; or alternatively, from 10 wt. % to 30 wt. % binder. These weight percentages are based on the total weight of the respective catalyst.

It is worth noting that chromium polymerization catalysts usually require chromium loadings in a rather narrow range, typically from 0.5 to 2 wt. %, because higher amounts cannot be converted into Cr(VI) at the usual calcination temperatures required by polymerization catalysts. Higher values can also degrade the polymer and lower amounts result in low activity. However, no such limitation exists in the present invention. Thus, the amount of chromium in the supported chromium catalyst (or the reduced chromium catalyst) typically can range from 0.01 to 50 wt. %; alternatively, from 0.01 to 10 wt. %; alternatively, from 0.05 to 15 wt. %; alternatively, from 0.1 to 5 wt. %; alternatively, from 0.2 to 10 wt. %; alternatively, from 0.5 to 30 wt. %; or alternatively, from 1 to 10 wt. % of chromium. These weight percentages are based on the amount of chromium relative to the total weight of the respective catalyst. While not wishing to be bound by theory, it is believed that lower chromium loadings (e.g., 1 wt. % and less) can result in higher selectivity to methanol, while higher chromium loadings (e.g., 5-10 wt. % or 10-20 wt. %) can result in higher methanol yields per gram of catalyst.

Likewise, the reduced chromium catalyst (in step (a) of the second process), and which has an average oxidation state of +5 or less, is not particularly limited in the amount of chromium it contains, and it can fall within the same ranges. Thus, upon conclusion of the reduction step, the reduced chromium catalyst can contain from 0.01 to 50 wt. %, from 0.01 to 10 wt. %, from 0.05 to 15 wt. %, from 0.1 to 5 wt. %, from 0.2 to 10 wt. %, from 0.5 to 30 wt. %, or from 1 to 10 wt. % of chromium in an average oxidation state of +5 or less, based on the total weight of the reduced chromium catalyst.

Generally, at least 10 wt. % of the chromium in the supported chromium catalyst (in step (i) of the first process and/or in step (a) of the second process) is present in a hexavalent oxidation state before the reduction or contacting step, and more often at least 20 wt. % is present as chromium (VI). In further aspects, at least 40 wt. %, at least 60 wt. %, at least 80 wt. %, at least 90 wt. %, or at least 95 wt. %, of the chromium in the supported chromium catalyst can be present in an oxidation state of +6. These weight percentages are based on the total amount of chromium. Traditional chromium (VI) catalysts often will have an orange, yellow, or tan color, indicating the presence of chromium (VI).

Conversely, less than or equal to 70 wt. % of the chromium in the reduced chromium catalyst (in the second process) is typically present in an oxidation state of +6 (VI), and more often, less than or equal to 50 wt. %, or less than or equal to 40 wt. %. In further aspects, less than or equal to 30 wt. %, or less than or equal to 15 wt. % of chromium in the reduced chromium catalyst can be present in an oxidation state of +6. The minimum amount of chromium (VI) often can be 0 wt. % (no measurable amount), at least 0.5 wt. %, at least 1 wt. %, at least 2 wt. %, or at least 5 wt.

%. These weight percentages are based on the total amount of chromium. The reduced chromium catalysts often will have a green, blue, gray, or black color.

Thus, in the second process and when oxygen is not added in step (a), the irradiation and contacting of the supported chromium catalyst with the methane reactant ordinarily results in at least 10 wt. %, at least 20 wt. %, at least 40 wt. %, at least 60 wt. %, at least 80 wt. %, or at least 90 wt. %, of the supported chromium catalyst being reduced or converted to form the reduced chromium catalyst in step (a) of the second process when oxygen is not present.

Additionally or alternatively, the chromium in the reduced chromium catalyst (in step (a) of the second process in the absence of oxygen) can be characterized by an average valence of less than or equal to 5.25. More often, the chromium in the reduced chromium catalyst has an average valence of less than or equal to 5; alternatively, an average valence of less than or equal to 4.75; alternatively, an average valence of less than or equal to 4.5; alternatively, an average valence of less than or equal to 4.25; or alternatively, an average valence of less than or equal to 4. When the oxygen is added during reduction, these valences may not be reached due to the presence of oxygen. Average valence can be determined using the procedure described in U.S. Patent Publication No. 2020/0086307.

It is important to note that chromium polymerization catalysts require supports of high porosity so as to allow fragmentation of the catalyst and subsequent egress of the polymer chains from the fragments, which are hundreds of times longer than the pore diameter in the catalyst. However, in the present invention, no such restriction exists. Thus, the total pore volume of the supported chromium catalyst (or the reduced chromium catalyst) is not particularly limited. For instance, the supported chromium catalyst (or the reduced chromium catalyst) can have a total pore volume in a range from 0.1 to 5 mL/g, from 0.15 to 5 mL/g, from 0.1 to 3 mL/g, from 0.15 to 2 mL/g, from 0.1 to 1 mL/g, or from 0.5 to 1.0 mL/g. Low pore volume supports and low pore volume supported chromium catalysts can be used herein, with total pore volumes less than 1 mL/g, such as in the 0.1-0.5 mL/g range.

Likewise, the surface area of the supported chromium catalyst (or the reduced chromium catalyst) is not limited to any particular range. Generally, however, the supported chromium catalyst (or the reduced chromium catalyst) can have a BET surface area in a range from 50 to 2000 m$^2$/g, from 50 to 700 m$^2$/g, from 300 to 200 m$^2$/g, from 400 to 1200 m$^2$/g, or from 750 to 2000 m$^2$/g. High BET surface area supports and high BET surface area supported chromium catalysts can be used herein, with BET surface areas greater than 500 m$^2$/g or greater than 700 m$^2$/g, such as in the 1000-2000 m$^2$/g range. With high surface area, there can be high chromium (and hexavalent chromium) content. For instance, low pore volume and high BET surface area chromium/silica catalysts can be used.

The supported chromium catalyst (or the reduced chromium catalyst) can have any suitable shape or form, and such can depend on the type of process that is employed to convert the methane into methanol (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadrilobe, ring, wagon wheel, monolith, and the like, as well as any combination thereof. Accordingly, various methods can be utilized to prepare the supported chromium catalyst particles, including, for example, extrusion, spray drying, pelletizing, marumerizing, spherodizing, agglomeration, oil drop, and the like, as well as combinations thereof.

In some aspects, the supported chromium catalyst (or the reduced chromium catalyst) has a relatively small particle size, in which representative ranges for the average (d50) particle size of the catalyst can include from 10 to 500 microns, from 25 to 250 microns, from 20 to 100 microns, from 40 to 160 microns, or from 40 to 120 microns.

In other aspects, the supported chromium catalyst (or the reduced chromium catalyst) can be in the form of pellets or beads—and the like—having an average size ranging from 1/16 inch to 1/2 inch, or from 1/8 inch to 1/4 inch. As noted above, the size of the catalyst particles can be varied to suit the particular process for converting the methane reactant into the methanol product. In general, smaller pellets or beads may be preferable in order to achieve maximum contact with the light.

Production Systems

A first methanol production system provided herein can comprise (I) a single fluidized bed reactor configured to produce a reaction mixture comprising methanol from methane and water in the presence of a supported chromium catalyst in an oxidizing atmosphere, wherein the reactor comprises a source of a light beam at a wavelength in the UV-visible spectrum, (II) a separations system configured to isolate methanol from a reactor effluent discharged from the reactor, and (III) a recycle system configured to convey unreacted methane, water, and oxygen (e.g., air) back to the reactor. The first system also can include (IV) an activation vessel configured to regenerate at least a portion of the supported chromium catalyst. The recycle system can be further configured to convey this portion of the regenerated supported chromium catalyst back to the reactor.

A second methanol production system provided herein can comprise (A) a first fluidized bed reactor configured to produce a reduced chromium catalyst from methane in the presence of a supported chromium catalyst, optionally in an oxidizing atmosphere, wherein the reactor comprises a source of a light beam at a wavelength in the UV-visible spectrum, (B) a second fluidized bed reactor configured to produce a reaction mixture comprising methanol from the reduced chromium catalyst and water, optionally in an oxidizing atmosphere, (C) a separations system configured to isolate methanol from a reactor effluent discharged from the second reactor, and (D) a recycle system configured to convey unreacted methane, water, and oxygen (e.g., air) back to the first fluidized bed reactor or the second fluidized bed reactor. The second system also can include (E) an activation vessel configured to regenerate at least a portion of the supported chromium catalyst, e.g., by calcining the reduced chromium catalyst in an oxidizing atmosphere. The recycle system can be further configured to convey this portion of the regenerated supported chromium catalyst back to the reactor.

Generally, the features of the first production system and the second production system are the same as those described generally herein for the respective first process and second process. Thus, any features of the first process and the second process can be applied to the respective first production system and the second production system. For instance, each reactor (the single fluidized bed reactor, the first fluidized bed reactor, and the second fluidized bed reactor) can be configured to operate at a temperature of less than or equal to 300° C., a pressure in a range from 5 to 1000 psig (34 to 6895 kPa), an average contact time in a range from 3 sec to 150 sec, and/or a WHSV in a range from 0.01 to 500 $hr^{-1}$.

While not being limited thereto, the single reactor in the first system and the first reactor in the second system can have one or more immersion lamps as a source of the light beam attached to the top, or attached to the bottom, or attached to the wall, or positioned in the wall of the respective reactor, or any combination of these locations. Additionally or alternatively, the single reactor in the first system and the first reactor in the second system can have one or more internal light sources of the light beam (e.g., immersion lamps) in the interior of the respective reactor. The internal light sources can enter the respective reactor through a port (one or more) positioned at a side/wall of the reactor.

Optionally, the first production system (or the second production system) can further comprise a back-up reactor for each respective reactor, the back-up reactor positioned in parallel with the respective reactor. The back-up reactor can be used when the single reactor (or the first reactor, or the second reactor) is out of service for maintenance, for catalyst regeneration, and so forth. Alternatively, the back-up reactor can be used simultaneously with the single reactor and/or the first reactor to allow for reduced production losses when a reactor is out of service for maintenance, for catalyst regeneration, and so forth. The back-up reactor is often positioned in parallel, such that swapping from one to other is relatively easy.

In the first production system, the separations system is configured to isolate methanol from a reactor effluent discharged from the single reactor, and in the second production system, the separations system is configured to isolate methanol from a reactor effluent discharged from the second reactor. The separations system in both the first and second production systems can comprise a condenser, which can be configured to separate a reaction product comprising methanol from the reactor effluent. The separations system also can comprise a distillation column, which can be configured to separate methanol from the reaction product (or from the reactor effluent).

Both the first and second production systems, optionally, can further include an activation vessel configured to regenerate (or re-oxidize) at least a portion of the supported chromium catalyst. Then, the regenerated or re-oxidized supported chromium catalyst can be re-used in the single fluidized bed reactor in the first production system and the first fluidized bed reactor in the second production system.

Referring now to FIG. 1, which illustrates first methanol production system 100 consistent with an aspect of the present disclosure. System 100 can include fluidized bed reactor 125, condenser 160, and distillation column 175. In FIG. 1, air feed stream 105 (as a source of oxygen for the oxidizing atmosphere in the reactor), water feed stream 110 (which can be in the form of steam or water vapor), and methane feed stream 115 are combined to form reactant feed stream 120 to fluidized bed reactor 125. Alternatively, air feed stream 105, water feed stream 110, and methane feed stream 115 can be fed separately to fluidized bed reactor 125, or any two of the individual reactants can be combined prior to entering fluidized bed reactor 125. Fluidized bed reactor 125 has one or more light beam sources 130, shown in FIG. 1 at the top and one side/wall of fluidized bed reactor 125.

Discharged from fluidized bed reactor 125 is reactor effluent 155, which enters condenser 160, and exiting condenser 160 are lights stream 165 and reaction product stream 170 (which contains methanol). The operating pressure and temperature of condenser 160 can be selected for optimum separations. Lights stream 165 can contain oxygen (e.g., air) and methane, and can be recycled back to reactant feed stream 120 and into fluidized bed reactor 125. If desired, lights stream 165 can be fractionated into a separate methane stream and oxygen/air stream for recycling.

Reaction product stream 170 in FIG. 1 enters distillation column 175 and is fractionated to isolate methanol product stream 180 and water stream 185. Water stream 185 can be recycled back to reactant feed stream 120 and into fluidized bed reactor 125.

Figure 2:
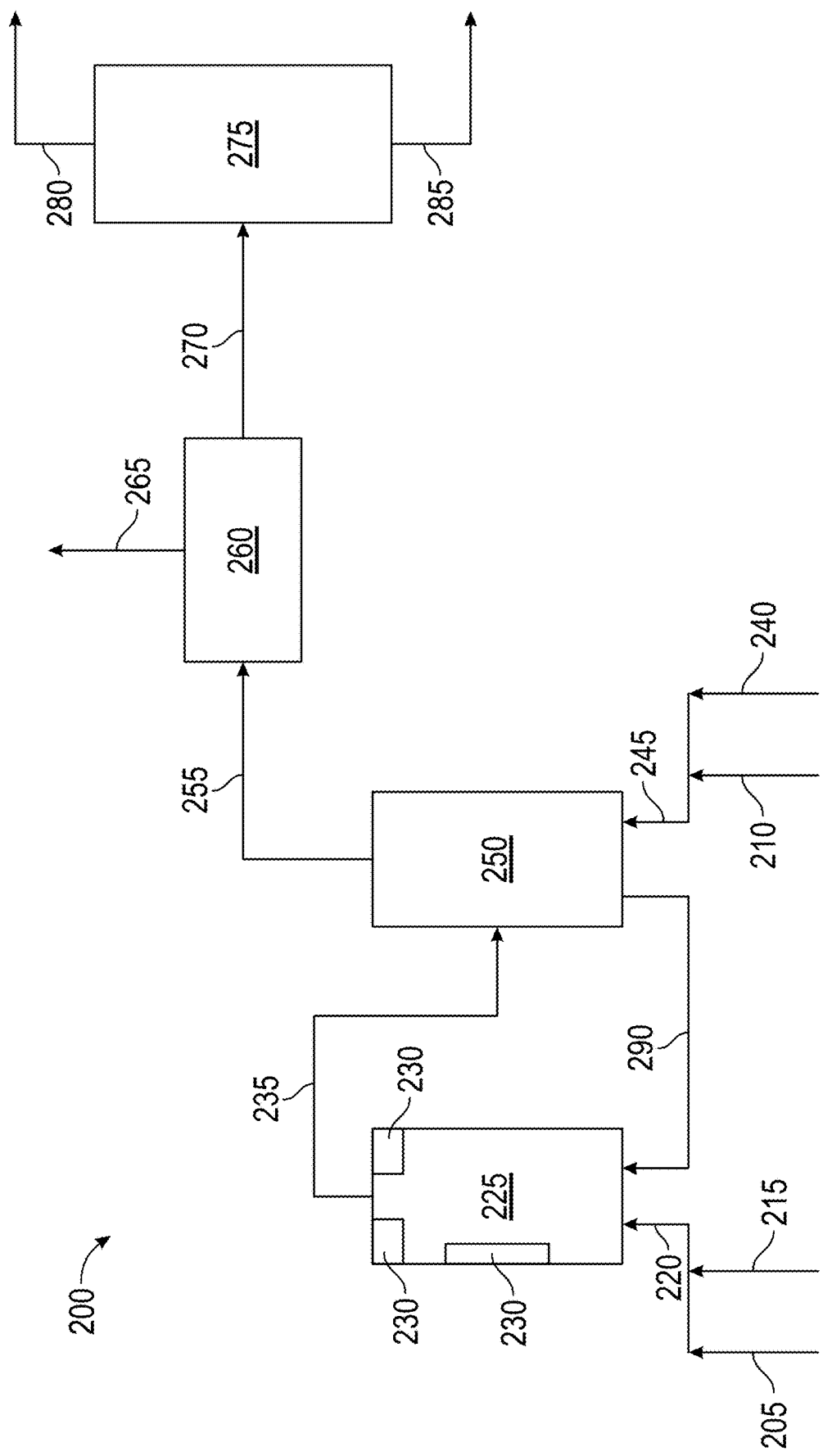
FIG. 2 illustrates a second methanol production system consistent with another aspect of the present disclosure.

Referring now to FIG. 2, which illustrates second methanol production system 200 consistent with an aspect of the present disclosure. System 200 can include first air feed stream 205 (as a source of oxygen for the oxidizing atmosphere), methane feed stream 215, first reactant feed stream 220, first fluidized bed reactor 225, one or more light beam sources 230, reactor effluent 255, condenser 260, lights stream 265, reaction product stream 270 (which contains methanol), distillation column 275, methanol product stream 280, and water stream 285, which are generally the same as described for the similarly numbered components in FIG. 1.

In FIG. 2, it is not required for an oxidizing atmosphere to be present in first fluidized bed reactor 225; thus, air feed stream 205 is not required. Discharged from first fluidized bed reactor 225 is intermediate stream 235 (which contains reduced chromium catalyst), which enters second fluidized bed reactor 250. Second air feed stream 240 (as a source of oxygen for the oxidizing atmosphere in the reactor) and water feed stream 210 (which can be in the form of steam or water vapor) are combined to form second reactor feed stream 245 to second fluidized bed reactor 250. Alternatively, second air feed stream 240 and water feed stream 210 can be fed separately to second fluidized bed reactor 250. In FIG. 2, it is not required for an oxidizing atmosphere to be present in second fluidized bed reactor 250; thus, second air feed stream 240 is not required.

From condenser 260, lights stream 265 can contain oxygen (e.g., air) and methane, and can be recycled back to first reactant feed stream 220 and into first fluidized bed reactor 225. If desired, lights stream 265 can be fractionated into a separate methane stream and oxygen/air stream for recycling. From distillation column 275, water stream 285 can be recycled back to second reactor feed stream 245 and into second fluidized bed reactor 250. Chromium catalyst recycle line 290 can convey chromium catalyst from second fluidized bed reactor 250 back to first fluidized bed reactor 225 for re-use. Optionally, an activation vessel (not shown) can regenerate or re-oxidize all or a portion of the chromium catalyst prior to use in first fluidized bed reactor 225.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

In Example 1, light-reduction was carried out in the absence of oxygen, and then oxygen was added at various temperatures to determine the optimum conditions that would be needed for reoxidation. The catalyst was 10 g of Cr/silica-titania (1 wt. % Cr, 4 wt. % Ti) with an average particle size was 130 microns. The catalyst was calcined in a fluidized bed (2-inch diameter quartz tube with sintered quartz frit as the distributor plate) at 800° C. in air that had been previously dried through a 13× molecular sieve column. The linear air velocity was 0.05 ft/sec. The ramp rate was 400° C. per hour and the hold time was 3 hr. After calcination, the temperature was rapidly cooled to 25° C. and the air was purged with similarly-dried nitrogen for 30 min. Afterward, the catalyst was captured and stored under nitrogen without any exposure to ambient air.

Then, the catalyst was placed in a glass bottle and light-reduced with a hydrocarbon. For convenience, 5 mL of isopentane was chosen to represent hydrocarbons in general (as described in U.S. Pat. No. 11,173,475). The catalyst and hydrocarbon were then gently rolled under UV light for 24 hr to achieve maximum reduction. The light beam was from two 60-watt 400 nm LED lamps located 2 inches away from the catalyst. During this treatment, the catalyst color changed from the original orange color to a light blue color, indicating full reduction.

Next, the catalyst was placed back into the 2-inch quartz tube under nitrogen and fluidized under nitrogen at 0.05 ft/sec. While the catalyst was still at 25° C., the gas stream was subsequently changed from nitrogen to wet air (air bubbled up through an 8-inch water column to reach saturated humidity) so that the alcohol would be hydrolyzed off the chromium and the reduced chromium could be re-oxidized. This caused an immediate color change back to a yellow-orange color, indicating reoxidation back to Cr(VI). However, when the tube was heated up to 100° C. the catalyst turned green, indicating reduction again, probably from the liberated alcohol product which was not volatile enough to evaporate at 25° C. Further heating caused a gradual reversion back to the yellow-orange color as the Cr was oxidized back to Cr(VI) and the products were evaporated away. When the temperature reached 350° C., the catalyst was completely orange, like the original Cr(VI) starting catalyst. This example demonstrated that the hydrolysis and oxidation reactions can be done simultaneously, as is indicated in the first process disclosed herein.

Other light-reduction experiments were carried out using other hydrocarbons, including methane, ethane, propane, isobutane, n-pentane, n-hexane, and 2-methylpentane, with other chromium catalysts including Cr/alumina, Cr/aluminophosphate, Cr/silica-alumina, Cr/silica, and the like, with chromium loadings of 0.25-5.0 wt. %, as described in U.S. Pat. No. 11,173,475. Constructive Example 2 is provided as a condensation of this large body of work.

In Constructive Example 2, a 2 g sample of the same Cr/silica-titania catalyst described in Example 1, after calcination in dry air at 800° C. for 3 hr, is placed in a 100 mL air-tight bottle equipped with a septum. The dry air is purged out with dry nitrogen, followed by a 100 mL injection of methane gas, which increases the total pressure to 2 atm. This constitutes a methane:chromium molar ratio of 11.6:1. Then, 0.053 g of liquid water is injected into the bottle, which causes an immediate color change from deep orange to more of a yellowish orange, indicating hydration of the chromium. The water:methane molar ratio is approximately 0.66:1 and the water:chromium molar ratio is approximately 7.7:1. Next, 20 mL of oxygen is injected, which raises the total pressure to about 2.2 atm. This results in an oxygen:methane molar ratio of 0.2:1 and an oxygen:chromium molar ratio of 2.3:1.

The bottle is then placed under UV light and allowed to gently roll for 2 hr. This rolling action allows the catalyst powder to gradually turn over, thus exposing all of the catalyst to the light. For the light exposure, the sample is placed in a box containing a UV light source, where the light consists of two ZMHA 60-watt LED ultraviolet lamps (380-420 nm) outputting a total of 9600 lumens or 250,000 lux. The catalyst samples are placed 1-2 inches away from the bulbs.

After 2 hr, 15 mL of deionized water is injected to capture the products. Analysis of the products is via a GC-MS procedure, with an Agilent® 6890 gas chromatograph having a flame-ionizing detector (FID). It uses a Restek® Stapilwax column (P/N 10658) designed specifically to separate and detect light oxygenates. Analysis of the water indicates only methanol as the product. This indicates that the reduction occurs even in the presence of water and oxygen, as specified in the first process. The quantity of methanol produced is approximately 3.2 moles of methanol per mole of chromium. Since this value is considerably higher than theoretical upper limit dictated by stoichiometry, e.g., a value of 2.0, it shows that the first process as described herein is indeed catalytic.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for converting methane into methanol, the process comprising: (i) contacting methane, water, and a supported chromium catalyst comprising chromium in a hexavalent oxidation state with a light beam at a wavelength in the UV-visible spectrum in an oxidizing atmosphere in a single reactor to form a reaction product comprising methanol, (ii) discharging a reactor effluent containing the reaction product from the single reactor, and (iii) separating methanol from the reaction product.

Aspect 2. A process for converting methane into methanol, the process comprising: (a) contacting methane and a supported chromium catalyst comprising chromium in a hexavalent oxidation state with a light beam at a wavelength in the UV-visible spectrum, optionally in an oxidizing atmosphere, in a first reactor to form a form a reduced chromium catalyst (e.g., with at least a portion of the chromium on the reduced chromium catalyst having at least one bonding site with a methoxy group), (b) contacting the reduced chromium catalyst with water, optionally in an oxidizing atmosphere, in a second reactor to form a reaction product comprising methanol, (c) discharging a reactor effluent containing the reaction product from the second reactor, and (d) separating methanol from the reaction product.

Aspect 3. The process defined in aspect 1 or 2, wherein the wavelength comprises a single wavelength or a range of wavelengths in the visible spectrum (from 380 nm to 780 nm).

Aspect 4. The process defined in aspect 1 or 2, wherein the wavelength comprises a single wavelength or a range of wavelengths in the 200 nm to 750 nm range.

Aspect 5. The process defined in aspect 1 or 2, wherein the wavelength comprises a single wavelength or a range of wavelengths in the 300 to 750 nm range, the 350 nm to 650 nm range, the 300 nm to 500 nm range, the 350 to 450 nm range, or the 300 nm to 400 nm range.

Aspect 6. The process defined in aspect 1 or 2, wherein the wavelength comprises a single wavelength or a range of wavelengths below 600 nm, below 500 nm, below 475 nm, below 450 nm, below 430 nm, or below 420 nm.

Aspect 7. The process defined in any one of aspects 1-6, wherein the wavelength is a single wavelength.

Aspect 8. The process defined in any one of aspects 1-6, wherein the wavelength is a range of wavelengths spanning at least 5 nm, at least 10 nm, at least 25 nm, or at least 50 nm, for instance, wavelength ranges spanning 5 to 50 nm, or spanning 5 to 25 nm.

Aspect 9. The process defined in any one of the preceding aspects, wherein the light beam has any suitable intensity or an intensity in any range disclosed herein, e.g., at least 500 lumens, at least 1000 lumens, at least 2000 lumens, at least 5000 lumens, at least 10,000 lumens, or at least 20,000 lumens.

Aspect 10. The process defined in any one of the preceding aspects, wherein the light beam is from a light source having any suitable power or any power disclosed herein, which can depend upon the size of the reactor, the number of bulbs or light sources utilized, the residence time and WHSV, among other variables.

Aspect 11. The process defined in any one of the preceding aspects, wherein the supported chromium catalyst is irradiated with any suitable illuminance or any illuminance disclosed herein, e.g., at least 100 lux, at least 500 lux, at least 1000 lux, at least 2000 lux, at least 5000 lux, at least 10,000 lux, at least 20,000 lux, at least 50,000 lux, or at least 100,000 lux.

Aspect 12. The process defined in any one of the preceding aspects, wherein the light beam is from a blue light source or a UV light source.

Aspect 13. The process defined in any one of the preceding aspects, wherein the supported chromium catalyst (or the reduced chromium catalyst) comprises any suitable amount of chromium or an amount in any range disclosed herein, e.g., from 0.01 to 50 wt. %, from 0.01 to 10 wt. %, from 0.05 to 15 wt. %, from 0.1 to 5 wt. %, from 0.2 to 10 wt. %, from 0.5 to 30 wt. %, or from 1 to 10 wt. % of chromium, based on the weight of the respective catalyst.

Aspect 14. The process defined in any one of aspects 2-13, wherein the reduced chromium catalyst in step (a) comprises any suitable amount of chromium in an average oxidation state of +5 or less, or an amount in any range disclosed herein, e.g., from 0.01 to 50 wt. %, from 0.01 to 10 wt. %, from 0.05 to 15 wt. %, from 0.1 to 5 wt. %, from 0.2 to 10 wt. %, from 0.5 to 30 wt. %, or from 1 to 10 wt. % of chromium in an average oxidation state of +5 or less, based on the weight of the reduced chromium catalyst.

Aspect 15. The process defined in any one of the preceding aspects, wherein the amount of the chromium of the supported chromium catalyst in a hexavalent oxidation state in step (i) or step (a) is at least 10 wt. %, at least 20 wt. %, at least 40 wt. %, at least 60 wt. %, at least 80 wt. %, or at least 90 wt. %, based on the total amount of chromium on the supported chromium catalyst, and/or the amount of chromium of the reduced chromium catalyst in a hexavalent oxidation state in step (a) is (from 0 wt. %, from 0.5 wt. %, from 1 wt. %, or from 2 wt. % to) less than or equal to 50 wt. %, less than or equal to 40 wt. %, less than or equal to 30 wt. %, or less than or equal to 15 wt. %, based on the total amount of chromium on the reduced chromium catalyst.

Aspect 16. The process defined in any one of aspects 2-15, wherein at least 10 wt. %, at least 20 wt. %, at least 40 wt. %, at least 60 wt. %, at least 80 wt. %, or at least 90 wt. %, of the supported chromium catalyst is reduced to form the reduced chromium catalyst in step (a), based on the total amount of the supported chromium catalyst.

Aspect 17. The process defined in any one of aspects 2-16, wherein the chromium of the reduced chromium catalyst in step (a) has an average valence of less than or equal to 5.5, less than or equal to 5.25, less than or equal to 5, less than or equal to 4.5, less than or equal to 4.25, or less than or equal to 4.

Aspect 18. The process defined in any one of aspects 1-17, wherein the supported chromium catalyst (or the reduced chromium catalyst) comprises any suitable solid oxide or any solid oxide disclosed herein, e.g., silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, alumina borate, silica-boria, aluminophosphate-silica, titania-zirconia, or any combination thereof.

Aspect 19. The process defined in any one of aspects 1-17, wherein the supported chromium catalyst (or the reduced chromium catalyst) comprises silica, silica-alumina, silica-coated alumina, silica-titania, silica-titania-magnesia, silica-zirconia, silica-magnesia, silica-boria, aluminophosphate-silica, alumina, alumina borate, or any combination thereof.

Aspect 20. The process defined in any one of aspects 1-17, wherein the supported chromium catalyst (or the reduced chromium catalyst) comprises a chemically-treated solid oxide comprising a solid oxide (e.g., as in aspect 18 or 19, such as silica, alumina, silica-alumina, silica-titania, silica-zirconia, silica-yttria, aluminophosphate, zirconia, titania, thoria, or stania) treated with an electron-withdrawing anion.

Aspect 21. The process defined in aspect 20, wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, or any combination thereof.

Aspect 22. The process defined in aspect 20 or 21, wherein the chemically-treated solid oxide contains from 1 to 30 wt. %, from 2 to 20 wt. %, from 2 to 15 wt. %, from 2 to 10 wt. %, or from 3 to 10 wt. %, of the electron-withdrawing anion, based on the total weight of the chemically-treated solid oxide.

Aspect 23. The process defined in any one of aspects 1-17, wherein the supported chromium catalyst (or the reduced chromium catalyst) comprises a chemically-treated solid oxide comprising fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 24. The process defined in any one of aspects 1-17, wherein the supported chromium catalyst (or the reduced chromium catalyst) comprises chromium/silica, chromium/silica-titania, chromium/silica-titaniamagnesia, chromium/silica-alumina, chromium/silica-coated alumina, chromium/aluminophosphate, chromium/alumina, chromium/alumina borate, or any combination thereof.

Aspect 25. The process defined in any one of aspects 1-17, wherein the supported chromium catalyst (or the reduced chromium catalyst) comprises chromium/silica-titania, and the respective catalyst comprises any suitable amount of titanium or an amount in any range disclosed herein, e.g., from 0.1 to 20 wt. %, from 0.5 to 15 wt. %, from 1 to 10 wt. %, or from 1 to 6 wt. %, based on the weight of the respective catalyst.

Aspect 26. The process defined in any one of aspects 1-17, wherein the supported chromium catalyst (or the reduced chromium catalyst) comprises chromium/sulfated alumina, chromium/fluorided alumina, chromium/fluorided silica-alumina, chromium/fluorided silica-coated alumina, or any combination thereof.

Aspect 27. The process defined in any one of aspects 1-17, wherein the supported chromium catalyst (or the reduced chromium catalyst) comprises a zeolite.

Aspect 28. The process defined in aspect 27, wherein the supported chromium catalyst (or the reduced chromium catalyst) comprises a medium pore zeolite, a large pore zeolite, or a combination thereof.

Aspect 29. The process defined in aspect 27, wherein the zeolite comprises a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, or a combination thereof.

Aspect 30. The process defined in aspect 27, wherein the supported chromium catalyst (or the reduced chromium catalyst) comprises an L-zeolite, a Y-zeolite, a mordenite, an omega zeolite, and/or a beta zeolite.

Aspect 31. The process defined in any one of aspects 27-30, wherein the supported chromium catalyst (or the reduced chromium catalyst) comprises the zeolite and any suitable amount of binder or an amount in any range disclosed herein, e.g., from 3 wt. % to 35 wt. %, or from 5 wt. % to 30 wt. % binder, based on the weight of the respective catalyst.

Aspect 32. The process defined in any one of the preceding aspects, wherein the supported chromium catalyst (or the reduced chromium catalyst) has any suitable pore volume (total) or a pore volume (total) in any range disclosed herein, e.g., from 0.1 to 5 mL/g, from 0.15 to 5 mL/g, from 0.1 to 3 mL/g, from 0.1 to 1 mL/g, from 0.1 to 0.5 mL/g, or from 0.5 to 1 mL/g.

Aspect 33. The process defined in any one of the preceding aspects, wherein the supported chromium catalyst (or the reduced chromium catalyst) has any suitable BET surface area or a BET surface area in any range disclosed herein, e.g., from 50 to 2000 $m^2/g$, from 50 to 700 $m^2/g$, from 300 to 200 $m^2/g$, from 400 to 1200 $m^2/g$, or from 750 to 2000 $m^2/g$.

Aspect 34. The process defined in any one of the preceding aspects, wherein the supported chromium catalyst (or the reduced chromium catalyst) is in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagon-wheel, monolith, or any combination thereof.

Aspect 35. The process defined in any one of aspects 1-34, wherein the supported chromium catalyst (or the reduced chromium catalyst) has any suitable average (d50) particle size or an average (d50) particle size in any range disclosed herein, e.g., from 10 to 500 microns, from 25 to 250 microns, or from 20 to 100 microns.

Aspect 36. The process defined in any one of aspects 1-34, wherein the supported chromium catalyst (or the reduced chromium catalyst) comprises pellets or beads having any suitable average size or an average size in any range disclosed herein, e.g., from 1/16 inch to 1/2 inch, or from 1/8 inch to 1/4 inch.

Aspect 37. The process defined in any one of the preceding aspects, wherein step (i) and/or step (a) and/or step (b) is/are conducted at any suitable temperature or any temperature disclosed herein, e.g., less than or equal to 300° C., less than or equal to 200° C., less than or equal to 100° C., from 100° C. to 300° C., from −100° C. to 100° C., from 0° C. to 100° C., from 20° C. to 250° C., or from 10° C. to 40° C.

Aspect 38. The process defined in any one of the preceding aspects, wherein the molar ratio of methane to chromium (of the supported chromium catalyst) is in any suitable range or any range disclosed herein, e.g., at least 0.25:1, at least 0.5:1, at least 1:1, at least 10:1, at least 100:1, at least 1000:1, or at least 10,000:1.

Aspect 39. The process defined in any one of the preceding aspects, wherein the oxidizing atmosphere comprises any suitable oxidizing atmosphere or any oxidizing atmosphere disclosed herein, e.g., oxygen, air, a mixture of air and an inert gas (such as nitrogen), a mixture of oxygen and an inert gas, NO, $NO_2$, $N_2O$, ozone, a halide oxide, $H_2O_2$, an organic peroxide, as well as combinations thereof.

Aspect 40. The process defined in any one of the preceding aspects, wherein the molar ratio of molecular oxygen or other oxidizing agent to chromium (of the supported chromium catalyst or reduced chromium catalyst) is in any suitable range or any range disclosed herein, e.g., at least 0.25:1, at least 0.5:1, at least 1:1, at least 2:1, at least 10:1, at least 100:1, at least 1000:1, or at least 10,000:1.

Aspect 41. The process defined in any one of the preceding aspects, wherein the molar ratio of water to chromium (of the supported chromium catalyst or the reduced chromium catalyst) is in any suitable range or any range disclosed herein, e.g., at least 0.25:1, at least 0.5:1, at least 1:1, at least 5:1, at least 10:1, at least 100:1, at least 1000:1, or at least 10,000:1.

Aspect 42. The process defined in any one of the preceding aspects, wherein step (i) and step (a) comprise contacting methane with a fluidized bed of the supported chromium catalyst while irradiating (methane is in the gas phase during step (i) and step (a)).

Aspect 43. The process defined in any one of the preceding aspects, wherein step (i) and step (a) and step (b) independently are conducted at any suitable pressure or any pressure disclosed herein, e.g., from 5 to 1000 psig (34 to 6895 kPa), from 10 to 100 psig (69 to 689 kPa), or from 20 to 250 psig (138 to 1723 kPa).

Aspect 44. The process defined in any one of the preceding aspects, wherein step (i) and step (a) comprise contacting methane with the supported chromium catalyst at any suitable WHSV or a WHSV in any range disclosed herein, e.g., from 0.01 hr-1 to 500 $hr^{-1}$, from 0.1 $hr^{-1}$ to 10 $hr^{-1}$, or from 0.5 $hr^{-1}$ to 3 $hr^{-1}$.

Aspect 45. The process defined in any one of the preceding aspects, wherein the single reactor and the first reactor are fluidized bed reactors.

Aspect 46. The process defined in any one of aspects 2-45, wherein the second reactor is a fluidized bed reactor.

Aspect 47. The process defined in any one of aspects 1-46, wherein the single reactor and the first reactor have one or more immersion lamps as a source of the light beam attached to the top, attached to the bottom, attached to the wall, or positioned in the wall of the respective reactor, or any combination thereof.

Aspect 48. The process defined in any one of aspects 1-46, wherein the single reactor and the first reactor have one or more internal light sources (e.g., immersion lamps) of the light beam, the internal light sources entering through a port (one or more) positioned at a side/wall of the respective reactor.

Aspect 49. The process defined in any one of aspects 1-48, wherein water is added via steam injection into the single reactor and the second reactor.

Aspect 50. The process defined in any one of aspects 2-49, wherein the oxidizing atmosphere is present in the first reactor, or the oxidizing atmosphere is present in the second reactor, or the oxidizing atmosphere is present in both the first reactor and the second reactor.

Aspect 51. The process defined in any one of the preceding aspects, wherein a conversion of methane (or a yield to methanol) is any percent conversion (or yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 52. The process defined in any one of the preceding aspects, wherein a single pass conversion of methane (or a single pass yield to methanol) is any single pass percent conversion (or single pass yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 53. The process defined in any one of the preceding aspects, wherein the yield to methanol per mole of chromium (VI) of the supported chromium catalyst is any molar ratio based on moles of chromium (VI) disclosed herein, e.g., at least 0.01, at least 0.025, at least 0.05, at least 0.1, or at least 0.25 moles (and up to 10, up to 8, up to 5, up to 3, up to 2, up to 1.5, or up to 1 mole) of methanol.

Aspect 54. The process defined in any one of the preceding aspects, wherein the reactor effluent comprises methanol, unreacted methane, reaction by-products (e.g., formic acid), steam/water, and oxygen (air).

Aspect 55. The process defined in any one of the preceding aspects, wherein the reaction product comprises methanol, reaction by-products (e.g., formic acid or formaldehyde and/or secondary addition products of formaldehyde), and water.

Aspect 56. The process defined in any one of the preceding aspects, further comprising a step of separating the reaction product from the reactor effluent using any suitable technique or any technique disclosed herein, e.g., condensing.

Aspect 57. The process defined in any one of the preceding aspects, further comprising a step of recycling unreacted methane and/or oxygen (air) from the reactor effluent to the single reactor or the first reactor.

Aspect 58. The process defined in any one of the preceding aspects, wherein the step of separating methanol from the reaction product comprises any suitable technique or any technique disclosed herein, e.g., extraction, filtration, evaporation, distillation, or any combination thereof.

Aspect 59. The process defined in any one of the preceding aspects, wherein the step of separating methanol from the reaction byproducts (e.g., formic acid, water, formaldehyde and its addition products) comprises distillation.

Aspect 60. The process defined in any one of aspects 54-59, further comprising a step of neutralizing formic acid (e.g., with a base) or converting formic acid to a non-corrosive compound (e.g., an ester).

Aspect 61. The process defined in any one of aspects 1-60, further comprising a step of calcining/activating the supported chromium catalyst or the reduced chromium catalyst to regenerate at least a portion of the supported chromium catalyst comprising chromium in a hexavalent oxidation state.

Aspect 62. The process defined in aspect 61, wherein calcining/activating comprises subjecting the supported chromium catalyst or the reduced chromium catalyst to an oxidizing atmosphere at any suitable peak temperature and time conditions or any peak temperature and time conditions disclosed herein, e.g., a peak temperature from 300° C. to 1000° C., from 500° C. to 900° C., or from 350° C. to 600° C., for a time period of from 1 min to 24 hr, from 1 hr to 12 hr, from 30 min to 8 hr, or from 1 hr to 3 hr.

Aspect 63. A methanol production system comprising: (I) a single fluidized bed reactor configured to produce a reaction mixture comprising methanol from methane and water in the presence of a supported chromium catalyst in an oxidizing atmosphere, wherein the reactor comprises a source of a light beam at a wavelength in the UV-visible spectrum, (II) a separations system configured to isolate methanol from a reactor effluent discharged from the reactor, and (III) a recycle system configured to convey unreacted methane, water, and oxygen/air back to the reactor.

Aspect 64. A methanol production system comprising: (A) a first fluidized bed reactor configured to produce a reduced chromium catalyst from methane in the presence of a supported chromium catalyst, optionally in an oxidizing atmosphere, wherein the reactor comprises a source of a light beam at a wavelength in the UV-visible spectrum, (B) a second fluidized bed reactor configured to produce a reaction mixture comprising methanol from the reduced chromium catalyst and water, optionally in an oxidizing atmosphere, (C) a separations system configured to isolate methanol from a reactor effluent discharged from the second reactor, and (D) a recycle system configured to convey unreacted methane, water, and oxygen/air back to the first fluidized bed reactor or the second fluidized bed reactor.

Aspect 65. The system defined in aspect 63 or 64, wherein each reactor is configured to operate at a temperature of less than or equal to 300° C., a pressure in a range from 5 to 1000 psig (34 to 6895 kPa), and a WHSV in a range from 0.01 to 500 $hr^{-1}$.

Aspect 66. The system defined in any one of aspects 63-65, wherein the single reactor and the first reactor have one or more immersion lamps as a source of the light beam attached to the top, attached to the bottom, attached to the wall, or positioned in the wall of the respective reactor, or any combination thereof.

Aspect 67. The system defined in any one of aspects 63-65, wherein the single reactor and the first reactor have one or more internal light sources (e.g., immersion lamps) of the light beam, the internal light sources entering through a port (one or more) positioned at a side/wall of the respective reactor.

Aspect 68. The system defined in any one of aspects 63-67, wherein the system further comprises a back-up reactor for each respective reactor, the back-up reactor positioned in parallel with the respective reactor.

Aspect 69. The system defined in any one of aspects 63-68, wherein the separations systems comprise a condenser configured to separate a reaction product comprising methanol from the reactor effluent.

Aspect 70. The system defined in any one of aspects 63-69, wherein the separations systems comprise a distillation column configured to separate methanol from the reaction product (or from the reactor effluent).

Aspect 71. The system defined in any one of aspects 63-70, wherein the system further comprises an activation vessel configured to regenerate at least a portion of the supported chromium catalyst.

We claim:

1. A process for converting methane into methanol, the process comprising:
   (a) contacting methane and a supported chromium catalyst comprising chromium in a hexavalent oxidation state with a light beam at a wavelength in the UV-visible spectrum, optionally in a first oxidizing atmosphere, in a first reactor to form a reduced chromium catalyst;
   (b) contacting the reduced chromium catalyst with water, optionally in a second oxidizing atmosphere, in a second reactor to form a reaction product comprising methanol;
   (c) discharging a reactor effluent containing the reaction product from the second reactor; and
   (d) separating methanol from the reaction product;
   wherein a molar ratio of water in step (b) to methane in step (a) is from 1:2 to 2:1.

2. The process of claim 1, wherein:
   chromium of the reduced chromium catalyst in step (a) has an average valence of less than or equal to 5;
   the first reactor and the second reactor are fluidized bed reactors;
   the first oxidizing atmosphere is present in step (a);
   the second oxidizing atmosphere is present in step (b); and
   the process further comprises a step of calcining the reduced chromium catalyst after step (b) to regenerate at least a portion of the supported chromium catalyst.

3. The process of claim 2, wherein;
   the light beam is from a blue light source or a UV light source;
   the light beam comprises wavelengths above 350 nm and below 450 nm;
   the methane and the supported chromium catalyst are irradiated with an illuminance of at least 10,000 lux; or
   any combination thereof.

4. The process of claim 2, wherein step (a) is conducted at:
   a temperature from 20° C. to 250° C.;
   a pressure from 10 to 200 psig; and
   an average contact time of the supported chromium catalyst with methane from 3 sec to 150 sec.

5. The process of claim 1, wherein:
   a molar ratio of methane to chromium of the supported chromium catalyst in step (a) is at least 10:1; and
   a molar ratio of water to chromium of the reduced chromium catalyst in step (b) is at least 5:1.

6. The process of claim 1, wherein step (a) comprises contacting methane with a fluidized bed of the supported chromium catalyst while irradiating.

7. The process of claim 6, wherein the supported chromium catalyst:
   has a pore volume from 0.1 to 1 mL/g and a BET surface area from 750 to 2000 $m^2/g$;
   contains from 1 to 10 wt. % chromium, based on the weight of the supported chromium catalyst;
   comprises a chromium/silica catalyst; or
   any combination thereof.

8. The process of claim 1, wherein a molar yield of methanol is from 0.25 to 100 moles of the methanol per mole of chromium (VI) of the supported chromium catalyst.

9. The process of claim 1, further comprising;
   a step of condensing to separate the reaction product from the reactor effluent, and wherein separating methanol from the reaction product comprises distillation;
   a step of recycling unreacted methane from the reactor effluent to the first reactor;
   a step of calcining the reduced chromium catalyst after step (b) to regenerate at least a portion of the supported chromium catalyst; or
   any combination thereof.

10. The process of claim 1, wherein the first reactor and the second reactor are fluidized bed reactors.

11. The process of claim 10, wherein water is added in step (b) via steam injection into the second reactor.

12. The process of claim 1, wherein the first reactor has one or more immersion lamps as a source of the light beam attached to a top, attached to a bottom, attached to a wall, or positioned in a wall of the first reactor, or any combination thereof.

13. The process of claim 1, wherein the first reactor has one or more internal light sources of the light beam, the internal light sources entering through one or more ports positioned at a wall of the first reactor.

14. The process of claim 1, wherein the reactor effluent comprises methanol, unreacted methane, and a reaction by-product comprising formic acid.

15. A process for converting methane into methanol, the process comprising:
   (a) contacting methane and a supported chromium catalyst comprising chromium in a hexavalent oxidation state with a light beam at a wavelength in the UV-visible spectrum, in a first oxidizing atmosphere comprising air and in a first reactor to form a reduced chromium catalyst, wherein a molar ratio of molecular oxygen in the first oxidizing atmosphere to methane is from 0.1:1 to 1:1;
   (b) contacting the reduced chromium catalyst with water, optionally in a second oxidizing atmosphere, in a second reactor to form a reaction product comprising methanol;
   (c) discharging a reactor effluent containing the reaction product from the second reactor; and
   (d) separating methanol from the reaction product.

16. The process of claim 15, wherein:
   chromium of the reduced chromium catalyst in step (a) has an average valence of less than or equal to 5;
   the first reactor and the second reactor are fluidized bed reactors;

the second oxidizing atmosphere is present in step (b); and the process further comprises a step of calcining the reduced chromium catalyst after step (b) to regenerate at least a portion of the supported chromium catalyst.

17. The process of claim 15, wherein:
the light beam is from a blue light source or a UV light source;
the light beam comprises wavelengths above 350 nm and below 450 nm;
the methane and the supported chromium catalyst are irradiated with an illuminance of at least 10,000 lux; or
any combination thereof.

18. The process of claim 15, wherein:
water is added in step (b) via steam injection into the second reactor;
step (a) comprises contacting methane with a fluidized bed of the supported chromium catalyst while irradiating; and
step (a) is conducted at:
a temperature from 20° C. to 250° C.;
a pressure from 10 to 200 psig; and
an average contact time of the supported chromium catalyst with methane from 3 sec to 150 sec.

19. The process of claim 15, wherein the supported chromium catalyst:
has a pore volume from 0.1 to 1 mL/g and a BET surface area from 750 to 2000 m$^2$/g;
contains from 1 to 10 wt. % chromium, based on the weight of the supported chromium catalyst; and
comprises a chromium/silica catalyst.

20. The process of claim 15, wherein:
a molar ratio of methane to chromium of the supported chromium catalyst in step (a) is at least 10:1;
a molar ratio of water to chromium of the reduced chromium catalyst in step (b) is at least 5:1; and
a molar yield of methanol is from 0.25 to 100 moles of the methanol per mole of chromium (VI) of the supported chromium catalyst.

21. The process of claim 15, further comprising:
a step of condensing to separate the reaction product from the reactor effluent, and wherein separating methanol from the reaction product comprises distillation;
a step of recycling unreacted methane from the reactor effluent to the first reactor;
a step of calcining the reduced chromium catalyst after step (b) to regenerate at least a portion of the supported chromium catalyst; or
any combination thereof.

22. The process of claim 15, wherein the first reactor has:
one or more immersion lamps as a source of the light beam attached to a top, attached to a bottom, attached to a wall, or positioned in a wall of the first reactor, or any combination thereof;
one or more internal light sources of the light beam, the internal light sources entering through one or more ports positioned at a wall of the first reactor; or
both.

23. A process for converting methane into methanol, the process comprising:
(a) contacting methane and a supported chromium catalyst comprising chromium in a hexavalent oxidation state with a light beam at a wavelength in the UV-visible spectrum, in a first oxidizing atmosphere comprising air and in a first reactor to form a reduced chromium catalyst, wherein a molar ratio of molecular oxygen in the first oxidizing atmosphere to chromium of the supported chromium catalyst is at least 2:1;
(b) contacting the reduced chromium catalyst with water, optionally in a second oxidizing atmosphere, in a second reactor to form a reaction product comprising methanol;
(c) discharging a reactor effluent containing the reaction product from the second reactor; and
(d) separating methanol from the reaction product.

24. The process of claim 23, wherein:
chromium of the reduced chromium catalyst in step (a) has an average valence of less than or equal to 5;
the first reactor and the second reactor are fluidized bed reactors;
the second oxidizing atmosphere is present in step (b);
the process further comprises a step of calcining the reduced chromium catalyst after step (b) to regenerate at least a portion of the supported chromium catalyst; and
the reactor effluent comprises methanol, unreacted methane, and a reaction by-product comprising formic acid.

25. The process of claim 23, wherein:
water is added in step (b) via steam injection into the second reactor;
step (a) comprises contacting methane with a fluidized bed of the supported chromium catalyst while irradiating; and
the supported chromium catalyst comprises a chromium/silica catalyst.

26. The process of claim 23, further comprising:
a step of condensing to separate the reaction product from the reactor effluent, and wherein separating methanol from the reaction product comprises distillation;
a step of recycling unreacted methane from the reactor effluent to the first reactor;
a step of calcining the reduced chromium catalyst after step (b) to regenerate at least a portion of the supported chromium catalyst; or
any combination thereof.

27. The process of claim 23, wherein the first reactor has:
one or more immersion lamps as a source of the light beam attached to a top, attached to a bottom, attached to a wall, or positioned in a wall of the first reactor, or any combination thereof;
one or more internal light sources of the light beam, the internal light sources entering through one or more ports positioned at a wall of the first reactor; or
both.

* * * * *